United States Patent
Lee et al.

(10) Patent No.: US 11,172,999 B2
(45) Date of Patent: Nov. 16, 2021

(54) ROLL JOINT MEMBER FOR SURGICAL INSTRUMENT

(71) Applicant: LIVSMED INC., Seongnam-si (KR)

(72) Inventors: Jung Joo Lee, Yongin-si (KR); Hee Jin Kim, Seongnam-si (KR); Jae Yeong Lee, Guri-si (KR); Min Ho Seo, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 318 days.

(21) Appl. No.: 16/190,839

(22) Filed: Nov. 14, 2018

(65) Prior Publication Data

US 2019/0142532 A1 May 16, 2019

(30) Foreign Application Priority Data

Nov. 14, 2017 (KR) .................. 10-2017-0151728

(51) Int. Cl.
*A61B 34/30* (2016.01)
*A61B 17/29* (2006.01)
*A61B 17/00* (2006.01)

(52) U.S. Cl.
CPC ........ *A61B 34/30* (2016.02); *A61B 17/00234* (2013.01); *A61B 2017/00314* (2013.01); *A61B 2017/2927* (2013.01); *A61B 2017/2929* (2013.01); *A61B 2034/305* (2016.02)

(58) Field of Classification Search
CPC ..... A61B 34/71; A61B 17/29; A61B 17/2909; A61B 17/295; A61B 2017/2901–2908; A61B 2017/291–2948; A61B 2017/2908; A61B 2017/00314; A61B 34/30; A61B 2034/301–306; A61B 2034/715; A61B 17/00234; A61B 17/28; A61B 17/2804; A61B 17/2812–282
See application file for complete search history.

(56) References Cited

U.S. PATENT DOCUMENTS

| | | | |
|---|---|---|---|
| 3,273,408 | A | 9/1966 | Nagel |
| 3,529,481 | A | 9/1970 | Budzyn |
| 5,478,347 | A | 12/1995 | Aranyi |
| 5,539,987 | A | 7/1996 | Zennyoji |
| 5,792,165 | A | 8/1998 | Klieman et al. |
| 5,797,900 | A | 8/1998 | Madhani et al. |
| 5,908,436 | A | 6/1999 | Cuschieri et al. |
| 5,954,731 | A | 9/1999 | Yoon |
| 6,191,017 | B1 | 2/2001 | Chittipeddi et al. |
| 6,394,998 | B1 | 5/2002 | Wallace et al. |
| 6,432,112 | B2 | 8/2002 | Brock et al. |
| 6,554,844 | B2 | 4/2003 | Lee et al. |
| 6,676,684 | B1 | 1/2004 | Morley et al. |
| 6,692,485 | B1 | 2/2004 | Brock et al. |

(Continued)

FOREIGN PATENT DOCUMENTS

| | | |
|---|---|---|
| JP | S59102587 A | 6/1984 |
| JP | 64-49739 A | 2/1989 |

(Continued)

*Primary Examiner* — Katherine H Schwiker
(74) *Attorney, Agent, or Firm* — Novick, Kim & Lee, PLLC; Sang Ho Lee

(57) ABSTRACT

Provided is a roll joint member for a surgical instrument. The roll joint member includes a wire guide portion, a guide member including a wire support portion, and a shaft member rotatably coupled to the guide member.

13 Claims, 18 Drawing Sheets

(56) References Cited

U.S. PATENT DOCUMENTS

| | | |
|---|---|---|
| 6,889,116 B2 | 5/2005 | Jinno |
| 6,936,042 B2 | 8/2005 | Wallace et al. |
| 6,969,385 B2 | 11/2005 | Moreyra |
| 6,994,716 B2 | 2/2006 | Jinno et al. |
| 7,101,363 B2 | 9/2006 | Nishizawa et al. |
| 7,338,513 B2 | 3/2008 | Lee et al. |
| 7,364,582 B2 | 4/2008 | Lee |
| 7,540,867 B2 | 6/2009 | Jinno et al. |
| 7,648,519 B2 | 1/2010 | Lee et al. |
| 7,686,826 B2 | 3/2010 | Lee et al. |
| 7,914,522 B2 | 3/2011 | Morley et al. |
| 7,942,895 B2 | 5/2011 | Jinno et al. |
| 8,100,824 B2 | 1/2012 | Hegeman et al. |
| 8,465,475 B2 | 6/2013 | Isbell, Jr. |
| 8,801,731 B2 | 8/2014 | Jeong |
| 8,821,480 B2 | 9/2014 | Burbank |
| 9,033,998 B1 | 5/2015 | Schaible et al. |
| 9,179,927 B2 | 11/2015 | Stefanchik et al. |
| 9,695,916 B2 | 7/2017 | Lee |
| 9,737,302 B2 | 8/2017 | Shelton, IV et al. |
| 10,105,128 B2 | 10/2018 | Cooper et al. |
| 10,166,082 B1 | 1/2019 | Hariri et al. |
| 10,405,936 B2 | 9/2019 | Awtar et al. |
| 2003/0036748 A1 | 2/2003 | Cooper et al. |
| 2004/0199147 A1 | 10/2004 | Nishizawa et al. |
| 2005/0096694 A1 | 5/2005 | Lee |
| 2006/0020287 A1 | 1/2006 | Lee |
| 2006/0025811 A1 | 2/2006 | Shelton, IV |
| 2006/0190034 A1 | 8/2006 | Nishizawa |
| 2006/0219065 A1 | 10/2006 | Jinno et al. |
| 2007/0208375 A1 | 9/2007 | Nishizawa |
| 2007/0265502 A1 | 11/2007 | Minosawa et al. |
| 2008/0000317 A1 | 1/2008 | Patton |
| 2008/0039255 A1 | 2/2008 | Jinno |
| 2008/0065116 A1 | 3/2008 | Lee et al. |
| 2008/0245175 A1 | 10/2008 | Jinno et al. |
| 2009/0112230 A1 | 4/2009 | Jinno |
| 2010/0160929 A1* | 6/2010 | Rogers ............... A61B 34/71 606/130 |
| 2010/0198253 A1 | 8/2010 | Jinno |
| 2010/0249818 A1 | 9/2010 | Jinno |
| 2010/0286480 A1 | 11/2010 | Peine et al. |
| 2011/0106145 A1 | 5/2011 | Jeong |
| 2011/0112517 A1 | 5/2011 | Peine |
| 2012/0004648 A1 | 1/2012 | Choi et al. |
| 2012/0303003 A1* | 11/2012 | Naito ................. A61B 17/29 606/1 |
| 2012/0330287 A1 | 12/2012 | Yim |
| 2013/0012958 A1 | 1/2013 | Marczyk et al. |
| 2013/0012959 A1 | 1/2013 | Jinno |
| 2013/0144274 A1 | 6/2013 | Stefanchik et al. |
| 2014/0114293 A1 | 4/2014 | Jeong et al. |
| 2014/0194893 A1 | 7/2014 | Jeong et al. |
| 2014/0318288 A1 | 10/2014 | Lee |
| 2014/0350570 A1 | 11/2014 | Lee |
| 2015/0032125 A1 | 1/2015 | Jeong et al. |
| 2015/0150635 A1 | 6/2015 | Kilroy et al. |
| 2016/0008068 A1 | 1/2016 | Hyodo et al. |
| 2016/0256232 A1 | 9/2016 | Awtar et al. |
| 2017/0042560 A1 | 2/2017 | Lee et al. |
| 2018/0110577 A1 | 4/2018 | Lee et al. |
| 2018/0228506 A1 | 8/2018 | Lee et al. |
| 2019/0336230 A1 | 11/2019 | Awtar et al. |

FOREIGN PATENT DOCUMENTS

| | | |
|---|---|---|
| JP | H06-311984 A | 11/1994 |
| JP | H08173442 A | 7/1996 |
| JP | 2004-122286 A | 4/2004 |
| JP | 2006-061364 A | 3/2006 |
| JP | 2006-062019 A | 3/2006 |
| JP | 2006-116194 A | 5/2006 |
| JP | 200634978 A | 9/2006 |
| JP | 2008-521485 A | 6/2008 |
| JP | 2010-220786 A | 10/2010 |
| JP | 4701433 B2 | 3/2011 |
| JP | 2011/521703 A | 7/2011 |
| JP | 2011-200666 A | 10/2011 |
| KR | 10-2006-0093060 A | 8/2006 |
| KR | 10-0695471 B1 | 3/2007 |
| KR | 10-2009-0119366 A | 11/2009 |
| KR | 10-2009-0124828 A | 12/2009 |
| KR | 10-0956501 B1 | 5/2010 |
| KR | 10-2010-0099818 A | 9/2010 |
| KR | 10-2010-0118573 A | 11/2010 |
| KR | 10-2011-0005671 A | 1/2011 |
| KR | 10-2011-0014534 A | 2/2011 |
| KR | 10-2011-0028613 A | 3/2011 |
| KR | 101064825 B1 | 9/2011 |
| KR | 10-1075294 B1 | 10/2011 |
| KR | 10-2012-0003091 A | 1/2012 |
| KR | 10-2013-0023311 A | 3/2013 |
| KR | 10-2013-0023755 A | 3/2013 |
| KR | 10-2013-0057250 A | 5/2013 |
| KR | 10-1301783 B1 | 8/2013 |
| KR | 10-1364970 B1 | 2/2014 |
| KR | 10-2014-0113893 A | 9/2014 |
| SN | 102131469 A | 7/2011 |
| WO | 2009/100366 A2 | 8/2009 |
| WO | 2009158115 A1 | 12/2009 |
| WO | 2010/030114 A2 | 3/2010 |
| WO | 2011/115311 A1 | 9/2011 |
| WO | 2012074564 A1 | 6/2012 |
| WO | 2013/077571 A1 | 5/2013 |
| WO | 2013082220 A2 | 6/2013 |
| WO | 2014/123390 A1 | 8/2014 |
| WO | 2014/156219 A1 | 10/2014 |

* cited by examiner

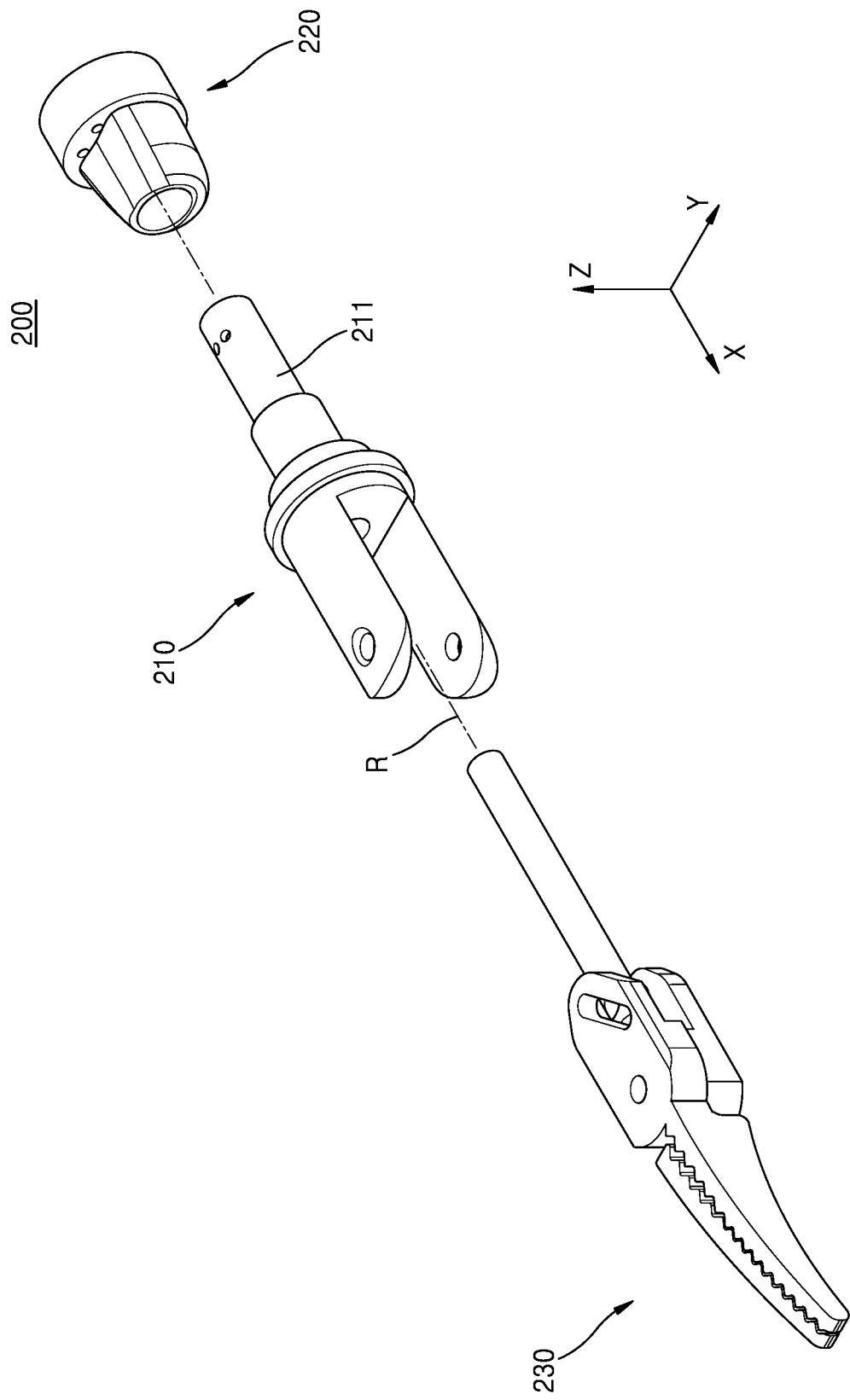

ROLL JOINT MEMBER FOR SURGICAL INSTRUMENT

CROSS-REFERENCE TO RELATED APPLICATION

This application claims priority to Korean Patent Application No. 10-2017-0151728, filed on Nov. 14, 2017, in the Korean Intellectual Property Office, the disclosure of which is incorporated herein in its entirety by reference.

BACKGROUND

1. Field

One or more embodiments relate to a roll joint member for a surgical instrument, and more particularly, to a roll joint member for a surgical instrument which improves the accuracy of a roll motion.

2. Description of the Related Art

Medical surgeries refer to heal diseases by cutting, incising, or manipulating skin, the mucous membrane, or other tissue by using medical devices. In particular, open surgeries, in which the skin at a surgical site is incised to open the body to treat, shape, or remove internal organs therein, may cause problems such as bleeding, side effects, pain, scars, and the like. Accordingly, surgeries, in which a certain hole is formed in the skin, and medical devices, for example, laparoscopes, surgical instruments, or microscopes for microsurgery, are inserted through the hole to conduct a surgery, or surgeries using robots have been highlighted as an alternative.

Surgical instruments are tools with which a surgeon conducts surgery at a surgical site by directly manipulating an end tool at one end of a shaft that passes through a hole punched in the skin, by hands using a certain operation unit, or by using a robot arm. The end tool provided in a surgical instrument may perform rotating, gripping, or cutting through a certain structure.

The above-described background technology is already possessed by the inventor to invent the present disclosure or technical information acquired in a process of the invention of the present disclosure, and cannot necessarily be said to be well-known technology open to the public prior to the filing of the present disclosure.

SUMMARY

One or more embodiments include a roll joint member for a surgical instrument which has improved accuracy of a roll motion.

Additional aspects will be set forth in part in the description which follows and, in part, will be apparent from the description, or may be learned by practice of the presented embodiments.

According to one or more embodiments, the present disclosure discloses a roll joint member for a surgical instrument which includes a wire guide portion, a guide member including a wire support portion, and a shaft member rotatably coupled to the guide member.

BRIEF DESCRIPTION OF THE DRAWINGS

These and/or other aspects will become apparent and more readily appreciated from the following description of the embodiments, taken in conjunction with the accompanying drawings in which:

FIG. 2A is an exploded perspective view of a roll joint member according to another embodiment;

DETAILED DESCRIPTION

Figure 1A:
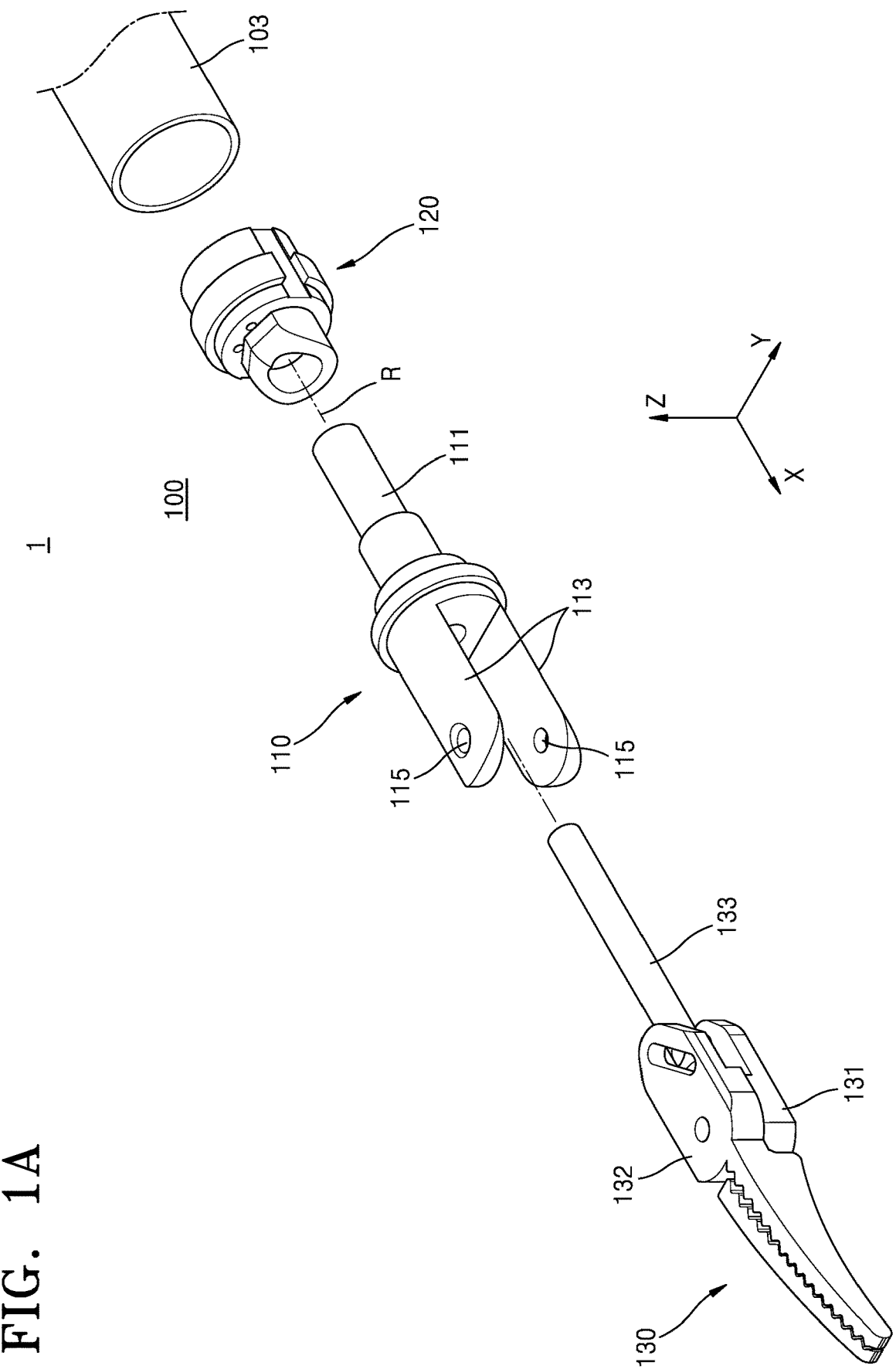
FIG. 1A is an exploded perspective view of a roll joint member according to an embodiment.

As the disclosure allows for various changes and numerous embodiments, embodiments will be illustrated in the drawings and described in detail in the written description. However, this is not intended to limit the present disclosure to particular modes of practice, and it is to be appreciated that all changes, equivalents, and substitutes that do not depart from the spirit and technical scope of the present disclosure are encompassed in the present disclosure. In the description of the present disclosure, certain detailed explanations of the related art are omitted when it is deemed that they may unnecessarily obscure the essence of the disclosure.

While such terms as "first," "second," etc., may be used to describe various components, such components must not be limited to the above terms. The above terms are used only to distinguish one component from another.

The terms used in the present specification are merely used to describe embodiments, and are not intended to limit the present disclosure. An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

The present disclosure will now be described more fully with reference to the accompanying drawings, in which embodiments of the disclosure are shown. Throughout the drawings, like reference numerals denote like elements. In the following description, when detailed descriptions about related well-known functions or structures are determined to make the gist of the present disclosure unclear, the detailed descriptions will be omitted herein.

Furthermore, in the description of various embodiments of the present disclosure, it is not necessary to independently interpreted or worked each embodiment, and technical concepts described in the respective embodiments should be understood to be interpreted or worked by being combined to another embodiment that is individually described Hereinafter, embodiments of the present disclosure are described below with reference to the accompanying drawings.

A surgical instrument 1 provided in a roll joint member according to an embodiment may include a roll joint member 100, an end tool 130, and a connection portion 103. The connection portion 103 has an empty shaft shape and may accommodate one or more wires to be described later therein. One end portion of the connection portion 103 is coupled to the end tool 130, and the other end portion thereof is coupled to a manipulation portion (not shown). Accordingly, the connection portion 103 may connect the end tool 130 to the manipulation portion. The manipulation portion may be a manipulation portion of a laparoscopic surgical tool or a driving portion of a surgical robot. Furthermore, the manipulation portion may be one of various members connected to the end tool 130 and capable of manipulating the end tool 130.

In the following description, various embodiments of the roll joint member 100 for guiding a roll motion of the end tool 130, which is formed between the end tool 130 and the connection portion 103 of the surgical instrument 1, are described in detail.

Figure 1B:
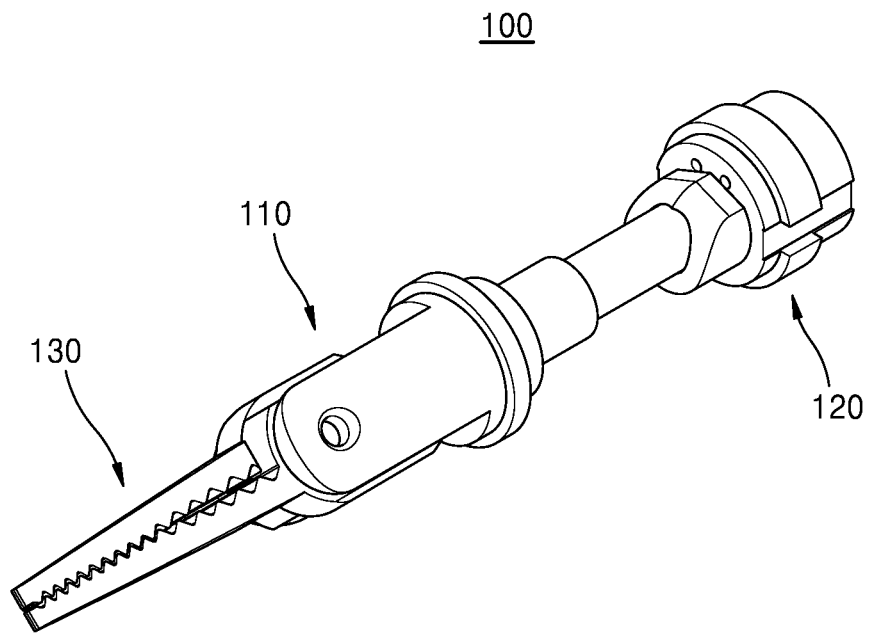
FIG. 1B is an assembled perspective view of the roll joint member of FIG. 1A.
Figure 1C:
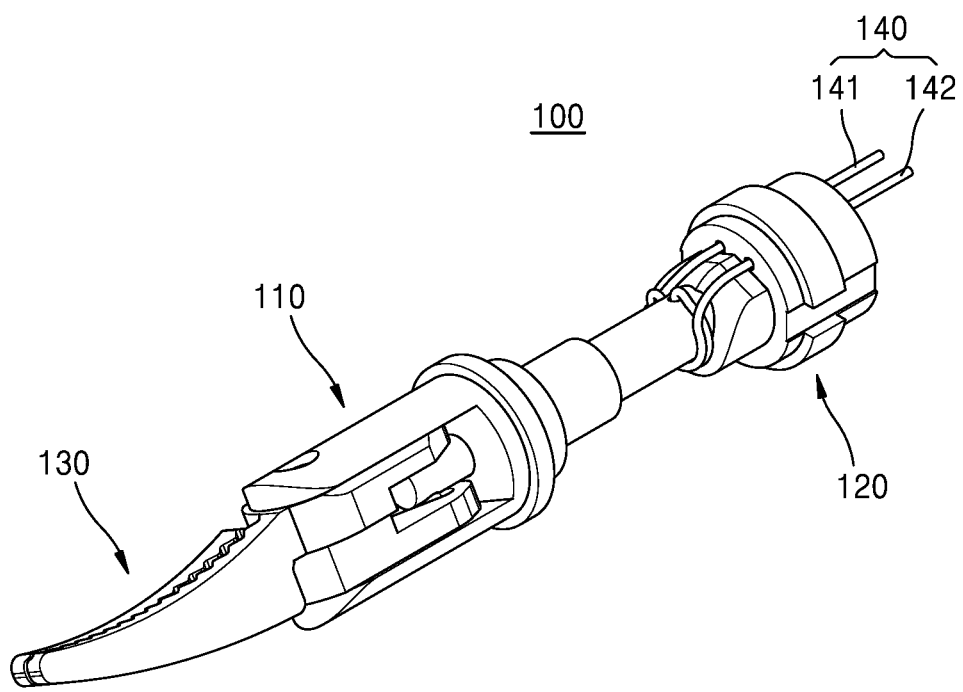
FIG. 1C is an assembled perspective view illustrating that a wire is coupled to the roll joint member of FIG. 1A.
Figure 1D:
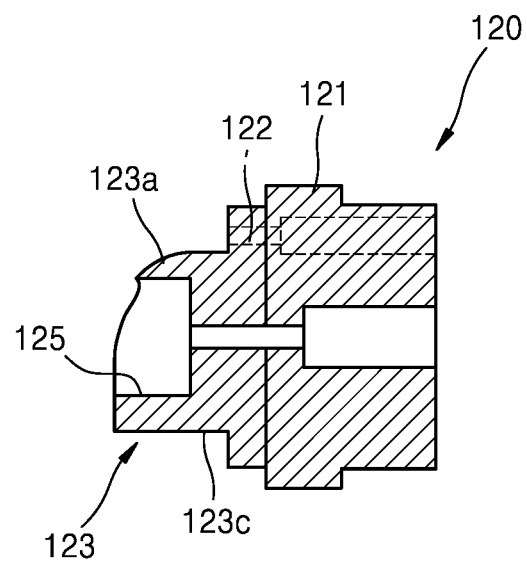
FIG. 1D is a lateral cross-sectional view of a guide member of the roll joint member of FIG. 1A.
Figure 1E:
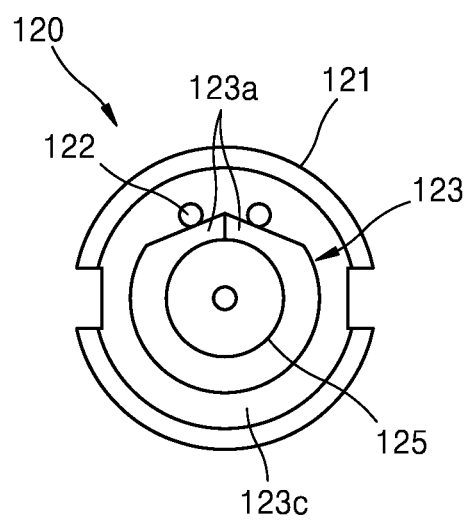
FIG. 1E is a front view of the guide member of the roll joint member of FIG. 1A.

FIG. 1A is an exploded perspective view of the roll joint member 100 according to an embodiment. FIG. 1B is an assembled perspective view of the roll joint member 100 of FIG. 1A. FIG. 1C is an assembled perspective view illustrating that a roll wire 140 is coupled to the roll joint member 100 of FIG. 1A. FIG. 1D is a lateral cross-sectional view of a guide member 120 of the roll joint member 100 of FIG. 1A. FIG. 1E is a front view of the guide member 120 of the roll joint member 100 of FIG. 1A.

Referring to FIGS. 1A to 1E, the roll joint member 100 for the surgical instrument 1 according to the present embodiment may include a shaft member 110 and the guide member 120. In this state, the end tool 130 is coupled to one end portion of the shaft member 110, and the connection portion 103 of the surgical instrument 1 is coupled to one end portion of the guide member 120. The roll wire 140 having one end portion fixedly coupled to the shaft member 110 penetrates the guide member 120 toward the connection portion 103 and the manipulation portion. In the following description, each of constituent elements is described in detail.

The roll wire 140 may include a first roll wire 141 and a second roll wire 142. The first roll wire 141 and the second roll wire 142 are separate wires, and one end portion of each of the first roll wire 141 and the second roll wire 142 may be fixedly coupled to the shaft member 110. Alternatively, the first roll wire 141 and the second roll wire 142 may be one wire (connected to each other), and a center point (or a connection point) may be fixedly coupled to the shaft member 110. In this state, although not illustrated, the roll wire 140 may be fixed to the shaft member 110 in various methods by using a hole or a groove, or by welding.

The shaft member 110 may include a shaft 111, an end tool receiving portion 113, and an end tool coupling portion 115.

The shaft 111 has a cylindrical shape and is inserted into the guide member 120. Accordingly, when the guide member 120 is in a fixed state, the shaft member 110 may be rotatable with respect to the guide member 120 along a roll axis R. In other words, a center axis of the shaft 111 may be the roll axis R.

The end tool receiving portion 113 has a shape of a pair of parallel plates, and may extend from the shaft 111 in a direction toward the end tool 130. The end tool coupling portion 115 may be further formed at an end portion of the end tool receiving portion 113 in a direction toward the end tool 130. In this state, the end tool coupling portion 115 may be formed in the form of a hole through which a coupling shaft (not shown) is inserted. In addition, the end tool coupling portion 115 may be formed in various shapes for coupling the shaft member 110 to the end tool 130.

The end tool 130 is accommodated in the end tool receiving portion 113. In detail, an end tool shaft 133 is accommodated in the shaft 111, and a first jaw 131 and a second jaw 132, which are coupled to the end tool shaft 133, are accommodated in the end tool receiving portion 113. In this state, the coupling shaft sequentially penetrates the end tool coupling portion 115 of the end tool receiving portion 113 and the first and second jaws 131 and 132, and thus the shaft member 110 and the end tool 130 may be coupled to each other.

The guide member 120 may include a housing 121 and a guide portion 123.

In this state, in the roll joint member 100 according to the present embodiment, the shaft member 110 and the guide member 120 are formed as separate members, and when the guide member 120 is in a fixed state, the shaft member 110 is characteristically formed to be rotatable with respect to the guide member 120.

In other words, in the case of a roll joint member according to the related art, generally, a shaft and a guide are integrally formed. In this case, since a wire wound around the shaft for a roll motion is also wound around the guide, the shaft and the guide form a rotational symmetry. In other words, to maintain the shape of the wire wound around the guide regardless of rotation of the shaft, the guide is formed in a rotational symmetry with respect to a shaft axis. Accordingly, the shape of the guide may be limited. Furthermore, it may be a problem that, as the guide rotates, a frictional force may be generated between the guide and the wire in a direction that is not a proceeding direction of the wire wound around the guide.

To address the above problem, in the roll joint member 100 according to the present embodiment, the shaft member 110 and the guide member 120 are formed as separate members, and when the guide member 120 is in a fixed state, the shaft member 110 is rotatable with respect to the guide member 120, as described in detail later.

The housing 121 has a hollow shape, and the guide portion 123 may be formed at one end portion of the housing 121 and the connection portion 103 of the surgical instrument 1 may be coupled to the other end portion of the housing 121.

One or more wire holes 122 may be formed in the housing 121. The wire holes 122 may be formed such the roll wire 140 may penetrate the wire holes 122, and the roll wire 140 may connect the end tool 130 with the manipulation portion. Although the drawings illustrate only the wire holes 122 that the roll wire 140 penetrates, the concept of the present disclosure is not limited thereto, and one or more wire holes that additional wires for other operations of the end tool 130 penetrate may be further formed in the housing 121.

The guide portion 123 may have a hollow shape. Accordingly, a shaft hole 125 may be formed in the housing 121 and the guide portion 123, and the shaft 111 of the shaft member 110 may be rotatably coupled to the shaft hole 125.

The guide portion 123 may include a wire guide portion 123a and a wire support portion 123c.

The wire guide portion 123a guides a path of the roll wire 140 that penetrates the wire holes 122.

The wire support portion 123c may support at least part of the roll wire 140. In other words, when the roll wire 140 wound around the shaft member 110 is wound around the wire guide portion 123a by changing a winding direction, the wire support portion 123c may support the roll wire 140 such that the roll wire 140 is stably wound around the shaft member 110.

Referring to FIGS. 1D and 1E, in the roll joint member 100 according to the present embodiment, the wire guide portion 123a and the wire support portion 123c are characteristically formed such that, when viewed on a plane perpendicular to the roll axis R, upper and lower sides (or left and right sides according to a rotation position) of the guide member 120 are asymmetrically formed with respect to the roll axis R. In other words, in FIG. 1E, with respect to a horizontal line including the roll axis R, the upper and lower sides of the guide member 120 are asymmetrically formed, and thus the upper and lower sides have different sections. In other words, the shaft member 110 and the guide member 120 are formed as separate members, and when the shaft member 110 does not rotate, the guide member 120 does not rotate, and thus the guide member 120 that does not rotate may be formed in an asymmetrical shape.

In this state, the wire guide portion 123a guides the path of the roll wire 140. The wire guide portion 123a may include two inclined surfaces forming a certain angle therebetween. The roll wire 140 having one end wound around the shaft member 110 is guided toward the wire holes 122 along the inclined surfaces of the wire guide portion 123a.

In this state, tension applied to the roll wire 140 allows the roll wire 140 to closely contact the inclined surfaces of the wire guide portion 123a. However, although the wire guide portion 123a is illustrated to be an inclined plane, when viewed on the plane perpendicular to the roll axis R, the wire guide portion 123a may be formed to be a curved surface having a certain curvature as a whole.

In contrast, the wire support portion 123c may be formed to be roughly a part of a cylinder, for example, in a semicircular shape, and may support at least a part of a portion of the roll wire 140 wound around the shaft member 110. In other words, the wire support portion 123c, when viewed on a plane perpendicular to the roll axis R, may have an arc shape having a certain central angle. As such, as the wire support portion 123c supports the roll wire 140 so that the roll wire 140 may be stably wound around the shaft member 110, linearity or stability of a roll motion may be improved. Furthermore, since the guide member 120 does not rotate and remains fixed during a roll motion, the roll wire 140 moves forward and backward only on the path of the roll wire 140 wound around the guide member 120, and thus a frictional force between the roll wire 140 and the guide member 120 may be reduced. In other words, an additional frictional force may not be generated because the guide member 120 does not rotate in a direction different from the direction in which the roll wire 140 moves forward or backward.

As such, as the shaft member 110 and the guide member 120 are formed as separate members, the shape of the guide member 120 may be asymmetrically formed without being limited by axis rotation symmetry. Accordingly, the shape of the guide member 120 may be manufactured according to an optimal path of the roll wire 140 suitable for the roll motion of the surgical instrument 1. Furthermore, when the roll wire 140 wound around the shaft member 110 is wound around the guide member 120 by changing the winding direction, the wire support portion 123c may support the roll wire 140 to be stably wound around the shaft member 110. Also, according to the above structure, the rotation of the shaft member 110 due to the roll motion may not affect the winding shape of the roll wire 140 wound around the guide member 120.

In this state, the driving principle of a roll motion using the roll wire 140 is as follows.

In a state in which one end portion of each of the first roll wire 141 and the second roll wire 142 which are provided as separate wires, or the center point (or connection point) when the first roll wire 141 and the second roll wire 142 form one wire, is fixed to the shaft member 110, the first roll wire 141 and the second roll wire 142 are wound around the shaft member 110, and a tension difference is applied to both sides of the first roll wire 141 and the second roll wire 142, that is, one side is pulled, and then the shaft member 110 is rotated as the first roll wire 141 and the second roll wire 142 are wound or released.

In this state, to guide the path of the roll wire 140, one or more wire holes may be formed in the guide member 120 as the wire holes 122. Accordingly, the roll wire 140 being fixed to and wound around the shaft member 110 may penetrate the wire holes 122 of the guide member 120 and extend in a direction opposite to the end tool 130. In this state, the guide portion 123 of the guide member 120 being fixed to and wound around the shaft member 110 may guide the roll wire 140 to proceed toward the wire holes 122 and simultaneously maintain the shape of the roll wire 140 being wound around the shaft member 110.

In other words, the wire guide portion 123a includes two inclined surfaces forming a certain angle, and tension applied to the roll wire 140 allows the roll wire 140 to closely contact the inclined surface of the wire guide portion 123a. The wire support portion 123c supports at least a part of the portion of the roll wire 140 wound around the shaft member 110.

According to the present embodiment, since the shaft member 110 and the guide member 120 are formed as separate members and the guide member 120 does not rotate even when the shaft member 110 rotates, the guide member 120 that does not rotate may be formed in an asymmetrical shape, and thus freedom of shape design may be much enhanced. Furthermore, since an asymmetrical shape is possible, the wire guide portion 123a, to which the roll wire 140 may be closely coupled, is formed at one side of the guide member 120, thereby stably guiding the path of the roll wire 140. Simultaneously, since the wire support portion 123c is formed at the other side of the guide member 120 to support the roll wire 140 being wound around the shaft member 110, linearity or stability of a roll motion may be improved. Furthermore, since the guide member 120 does not rotate and remains fixed during the roll motion of the shaft member 110, no frictional force is generated with respect to the roll wire 140 other than the forward and backward movements of the roll wire 140.

In the following description, a roll joint member 200 for the surgical instrument 1 according to another embodiment is described. In this state, the roll joint member 200 for the surgical instrument 1 according to the present embodiment is characteristically different from the roll joint member 100 for the surgical instrument 1 of FIG. 1A, in terms of the structure of a guide member 220. In the following description, the structure of the guide member 220 is mainly described below.

Figure 2B:
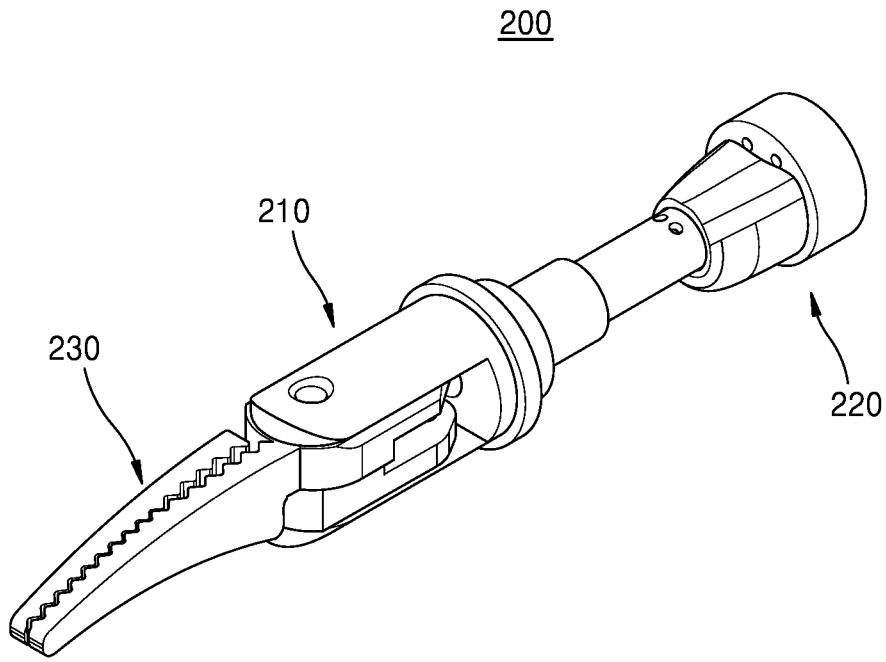
FIG. 2B is an assembled perspective view of the roll joint member of FIG. 2A.
Figure 2C:
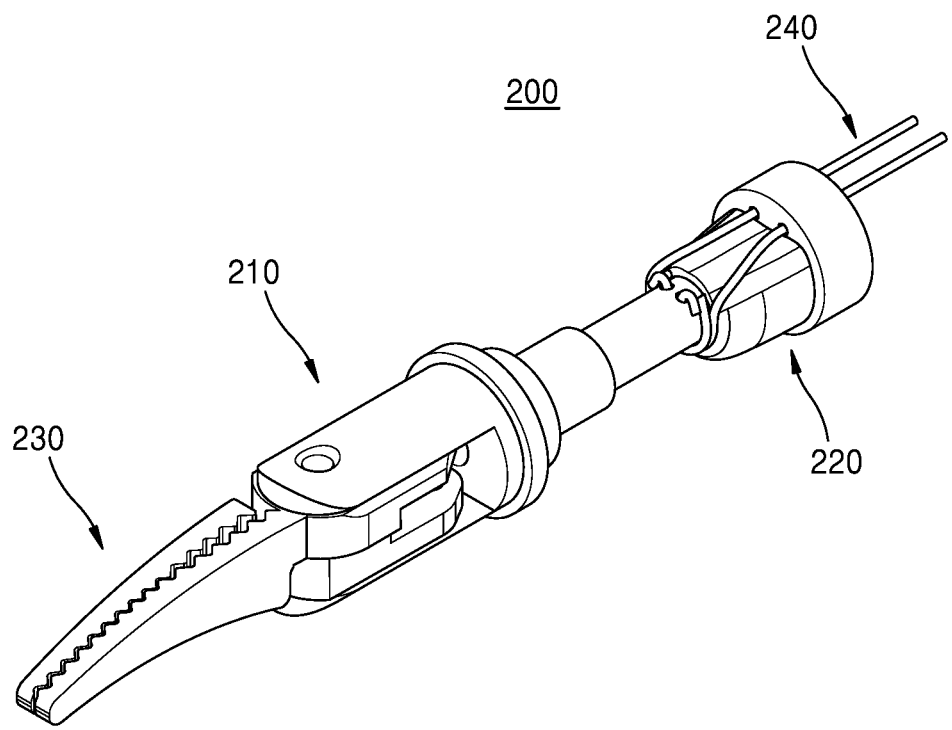
FIG. 2C is an assembled perspective view illustrating that a wire is coupled to the roll joint member of FIG. 2A.
Figure 2D:
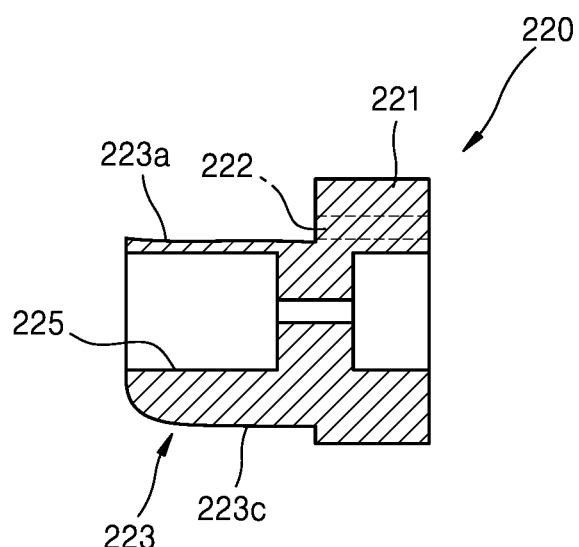
FIG. 2D is a lateral cross-sectional view of the guide member of the roll joint member of FIG. 2A.
Figure 2E:
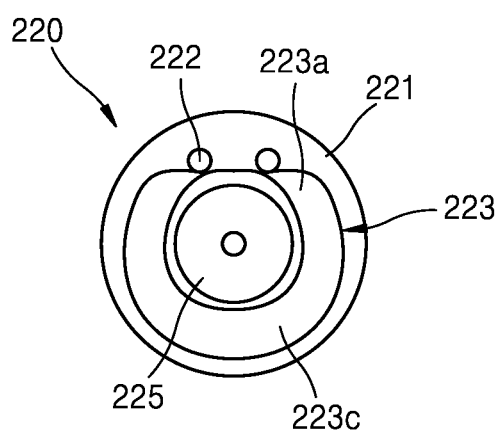
FIG. 2E is a front view of the guide member of the roll joint member of FIG. 2A.

FIG. 2A is an exploded perspective view of the roll joint member 200 according to another embodiment. FIG. 2B is an assembled perspective view of the roll joint member 200 of FIG. 2A. FIG. 2C is an assembled perspective view illustrating that a roll wire 240 is coupled to the roll joint member 200 of FIG. 2A. FIG. 2D is a lateral cross-sectional view of the guide member 220 of the roll joint member 200 of FIG. 2A. FIG. 2E is a front view of the guide member 220 of the roll joint member 200 of FIG. 2A.

Referring to FIGS. 2A to 2E, the roll joint member 200 for the surgical instrument 1 according to the present embodiment may include a shaft member 210 and the guide member 220. In this state, an end tool 230 is coupled to one end portion of the shaft member 210, and the connection portion 103 of FIG. 1 of the surgical instrument 1 is coupled to one end portion of the guide member 220. The roll wire 240 having the one end portion fixedly coupled to the shaft member 210 penetrates the guide member 220 and extends toward the connection portion 103 of FIG. 1 and the manipulation portion. In the following description, the guide member 220 is described in detail.

The guide member 220 may include a housing 221 and a guide portion 223.

The guide portion 223 may be formed in a hollow shape. Accordingly, a shaft hole 225 may be formed in the housing 221 and the guide portion 223, and a shaft 211 of the shaft member 210 may be rotatably coupled to the shaft hole 225.

The guide portion 223 may include a wire guide portion 223a and a wire support portion 223c.

The wire guide portion 223a guides a path of the roll wire 240 that penetrates a wire hole 222.

The wire support portion 223c may support at least a part of the roll wire 240. In other words, when the roll wire 240 wound around the shaft member 210 is wound around the wire guide portion 223a by changing a winding direction, the wire support portion 223c may support the roll wire 240 such that the roll wire 240 is stably wound around the shaft member 210.

Referring to FIGS. 2D and 2E, in the roll joint member 200 according to the present embodiment, the wire guide portion 223a and the wire support portion 223c are characteristically formed such that, when viewed on a plane perpendicular to the roll axis R, upper and lower sides (or left and right sides according to a rotation position) of the guide member 220 are asymmetrically formed with respect to the roll axis R. In other words, since the shaft member 210 and the guide member 220 are formed as separate members, even when the shaft member 210 rotates, the guide member 220 does not rotate, and thus the guide member 220 that does not rotate may be formed in an asymmetrical shape.

In this state, the wire guide portion 223a guides the path of the roll wire 240. The wire guide portion 223a may include a plane that is formed to be roughly flat. The roll wire 240 having one end portion wound around the shaft member 210 is guided toward the wire hole 222 along the plane of the wire guide portion 223a. In this state, tension applied to the roll wire 240 allows the roll wire 240 to closely contact a surface of the wire guide portion 223a. However, although the wire guide portion 223a is illustrated to be a flat plane, when viewed on a plane perpendicular to the roll axis R, the wire guide portion 223a may be formed in a free curved surface of various shapes.

In contrast, the wire support portion 223c is formed to be roughly a part of a cylinder, for example, in a hemispherical shape, and support at least a part of a portion of the roll wire 240 wound around the shaft member 210. As such, since the wire support portion 223c is provided to support the roll wire 240 so that the roll wire 240 is stably wound around the shaft member 210, linearity or stability of a roll motion may be improved. Furthermore, since the guide member 220 does not rotate and remains fixed during a roll motion, the roll wire 240 moves forward and backward only on the path of the roll wire 240 wound around the guide member 220, and thus a frictional force between the roll wire 240 and the guide member 220 may be reduced. In other words, an additional frictional force may not be generated because the guide member 220 does not rotate in a direction different from the direction in which the roll wire 240 moves forward or backward.

As such, since the shaft member 210 and the guide member 220 are formed as separate members, the shape of the guide member 220 may be asymmetrically formed without being limited by axial symmetry. Accordingly, the shape of the guide member 220 may be manufactured according to an optimal path of the roll wire 240 suitable for the roll motion of the surgical instrument 1. Furthermore, when the roll wire 240 wound around the shaft member 210 is wound around the guide member 220 by changing the winding direction, the wire support portion 223c may support the roll wire 240 to be stably wound around the shaft member 210. Also, according to the above structure, the rotation of the shaft member 210 due to the roll motion may not affect the winding shape of the roll wire 240 wound around the guide member 220.

In the following description, a roll joint member 300 for the surgical instrument 1 according to another embodiment is described below. In this state, the roll joint member 300 for the surgical instrument 1 according to the present embodiment is characteristically different from the roll joint member 100 for the surgical instrument 1 of FIG. 1A, in terms of the structure of a guide member 320. In the following description, the structure of the guide member 320 is mainly described below.

Figure 3A:
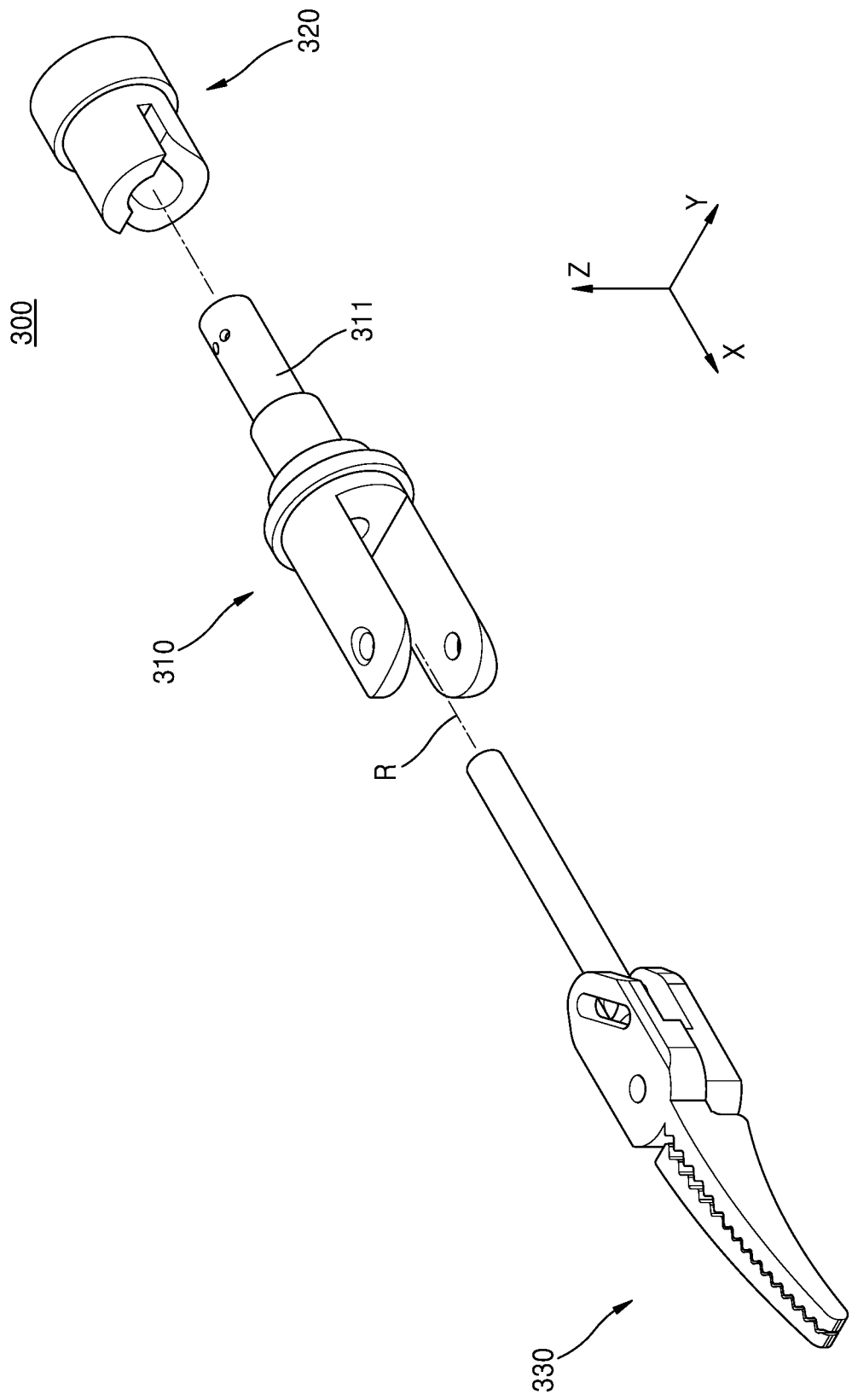
FIG. 3A is an exploded perspective view of a roll joint member according to another embodiment.
Figure 3B:
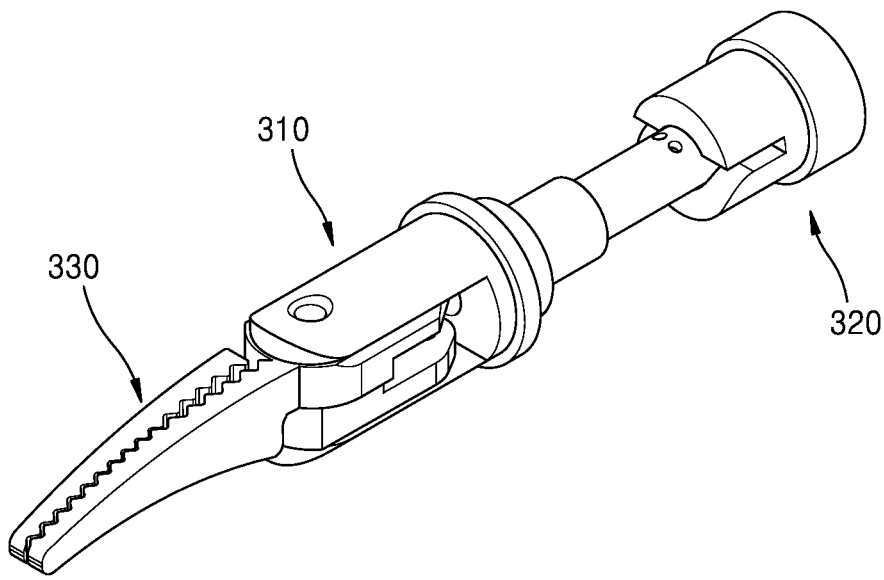
FIG. 3B is an assembled perspective view of the roll joint member of FIG. 3A.
Figure 3C:
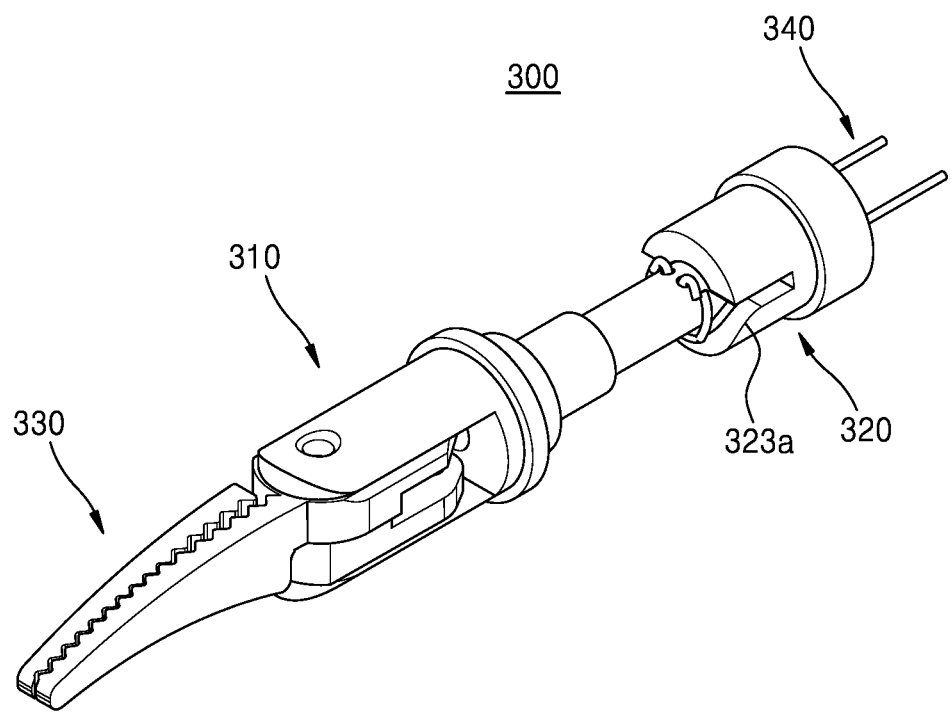
FIG. 3C is an assembled perspective view illustrating that a wire is coupled to the roll joint member of FIG. 3A.
Figure 3D:
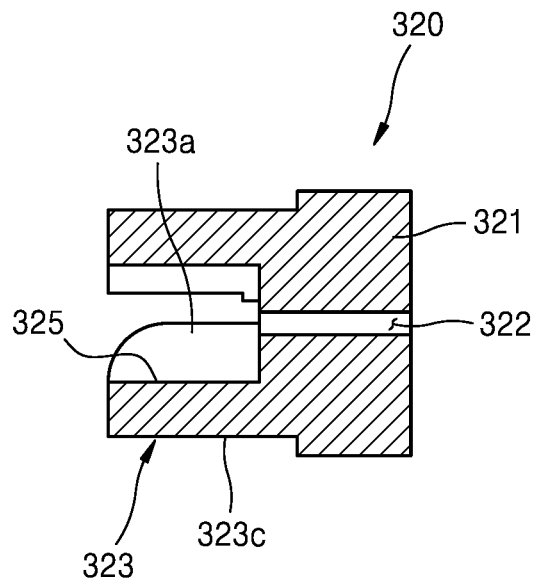
FIG. 3D is a lateral cross-sectional view of a guide member of the roll joint member of FIG. 3A.
Figure 3E:
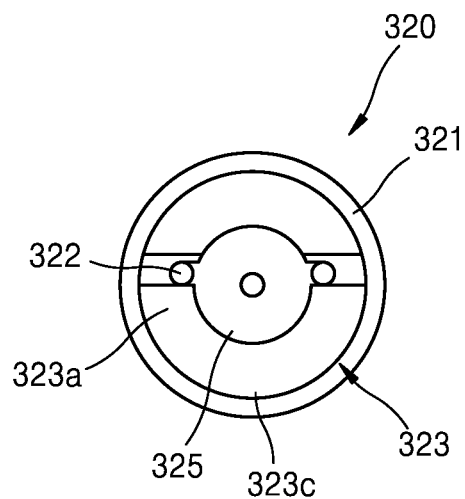
FIG. 3E is a front view of the guide member of the roll joint member of FIG. 3A.

FIG. 3A is an exploded perspective view of the roll joint member 300 according to another embodiment. FIG. 3B is an assembled perspective view of the roll joint member 300 of FIG. 3A. FIG. 3C is an assembled perspective view illustrating that a roll wire 340 is coupled to the roll joint member 300 of FIG. 3A. FIG. 3D is a lateral cross-sectional view of the guide member 320 of the roll joint member 300 of FIG. 3A. FIG. 3E is a front view of the guide member 320 of the roll joint member 300 of FIG. 3A.

Referring to FIGS. 3A to 3E, the roll joint member 300 for the surgical instrument 1 according to the present embodiment may include a shaft member 310 and a guide member 320. In this state, an end tool 330 is coupled to one end portion of the shaft member 310, and the connection portion 103 of the surgical instrument 1 of FIG. 1 is coupled to one end portion of the guide member 320. The roll wire 340 having one end portion fixedly coupled to the shaft member 310 penetrates the guide member 320 toward the connection portion 103 of FIG. 1 and the manipulation portion. In the following description, the guide member 320 is described in detail.

The guide member 320 may include a housing 321 and a guide portion 323.

The guide portion 323 may be formed in a hollow shape. Accordingly, a shaft hole 325 may be formed in the housing 321 and the guide portion 323, and a shaft 311 of the shaft member 310 may be rotatably coupled to the shaft hole 325.

The guide portion 323 may include a wire guide portion 323a and a wire support portion 323c.

The wire guide portion 323a guides a path of the roll wire 340 that penetrates a wire hole 322.

The wire support portion 323c may support at least a part of the roll wire 340. In other words, when the roll wire 340 wound around the shaft member 310 is wound around the wire guide portion 323a by changing a winding direction, the wire support portion 323c may support the roll wire 340 such that the roll wire 340 is stably wound around the shaft member 310.

Referring to FIGS. 3D and 3E, in the roll joint member 300 according to the present embodiment, the wire guide portion 323a and the wire support portion 323c are characteristically formed such that, when viewed on a plane perpendicular to the roll axis R, upper and lower sides (or left and right sides according to a rotation position) of the guide member 320 are asymmetrically formed with respect to the roll axis R. In other words, since the shaft member 310 and the guide member 320 are formed as separate members, even when the shaft member 310 rotates, the guide member 320 does not rotate, and thus the guide member 320 that does not rotate may be formed in an asymmetrical shape.

In this state, the wire guide portion 323a guides the path of the roll wire 340. The wire guide portion 323a may be formed in the form of a kind of channel. In other words, the wire guide portion 323a is formed to be inwardly recessed in a cylindrical shape, forming a certain curved surface therein along the path of the roll wire 340. In other words, when viewed on a sectional surface, a groove recessed to a certain degree in a direction along the roll axis R is generated. A surface forming the groove has a curved shape having a certain curvature, thereby forming the wire guide portion 323a. The roll wire 340 having one end portion wound around the shaft member 310 is guided toward the wire hole 322 along the curved surface of the wire guide portion 323a. In this state, tension applied to the roll wire 340 allows the roll wire 340 to closely contact the surface of the wire guide portion 323a.

In contrast, the wire support portion 323c is formed roughly in an arc shape under the wire guide portion 323a and may support at least a part of a portion of the roll wire 340 wound around the shaft member 310. As such, since the wire support portion 323c is provided to support the roll wire 340 so that the roll wire 340 may be stably wound around the shaft member 310, linearity or stability of a roll motion may be improved. Furthermore, since the guide member 320 does not rotate and remains fixed during a roll motion, the roll wire 340 moves forward and backward only on the path of the roll wire 340 wound around the guide member 320, and thus a frictional force between the roll wire 340 and the guide member 320 may be reduced. In other words, an additional frictional force may not be generated because the guide member 320 does not rotate in a direction different from the direction in which the roll wire 340 moves forward or backward.

In this state, although not illustrated, an arc portion of not only the lower side, but also the upper side of the wire support portion 323c may support the roll wire 340. In other words, although FIG. 3C does not illustrate that the upper arc portion supports the roll wire 340 because the shaft member 310 is in a default state, when the roll motion is performed on the shaft so that the wire hole 322 is placed on the side or lower surface, the roll wire 340 is supported by the upper arch portion.

As such, since the shaft member 310 and the guide member 320 are formed as separate members, the shape of the guide member 320 may be asymmetrically formed without being limited by axial symmetry. Accordingly, the shape of the guide member 320 may be manufactured according to an optimal path of the roll wire 340 suitable for the roll motion of the surgical instrument 1. Furthermore, when the roll wire 340 wound around the shaft member 310 is wound around the guide member 320 by changing the winding direction, the wire support portion 323c may support the roll wire 340 to be stably wound around the shaft member 310. Also, according to the above structure, the rotation of the shaft member 310 due to the roll motion may not affect the winding shape of the roll wire 340 wound around the guide member 320.

In the following description, a roll joint member 400 for the surgical instrument 1 according to another embodiment is described below. In this state, the roll joint member 400 for the surgical instrument 1 according to the present embodiment is characteristically different from the roll joint member 100 for the surgical instrument 1 of FIG. 1A, in terms of the structure of a guide member 420. In the following description, the structure of the guide member 420 is mainly described below.

Figure 4A:
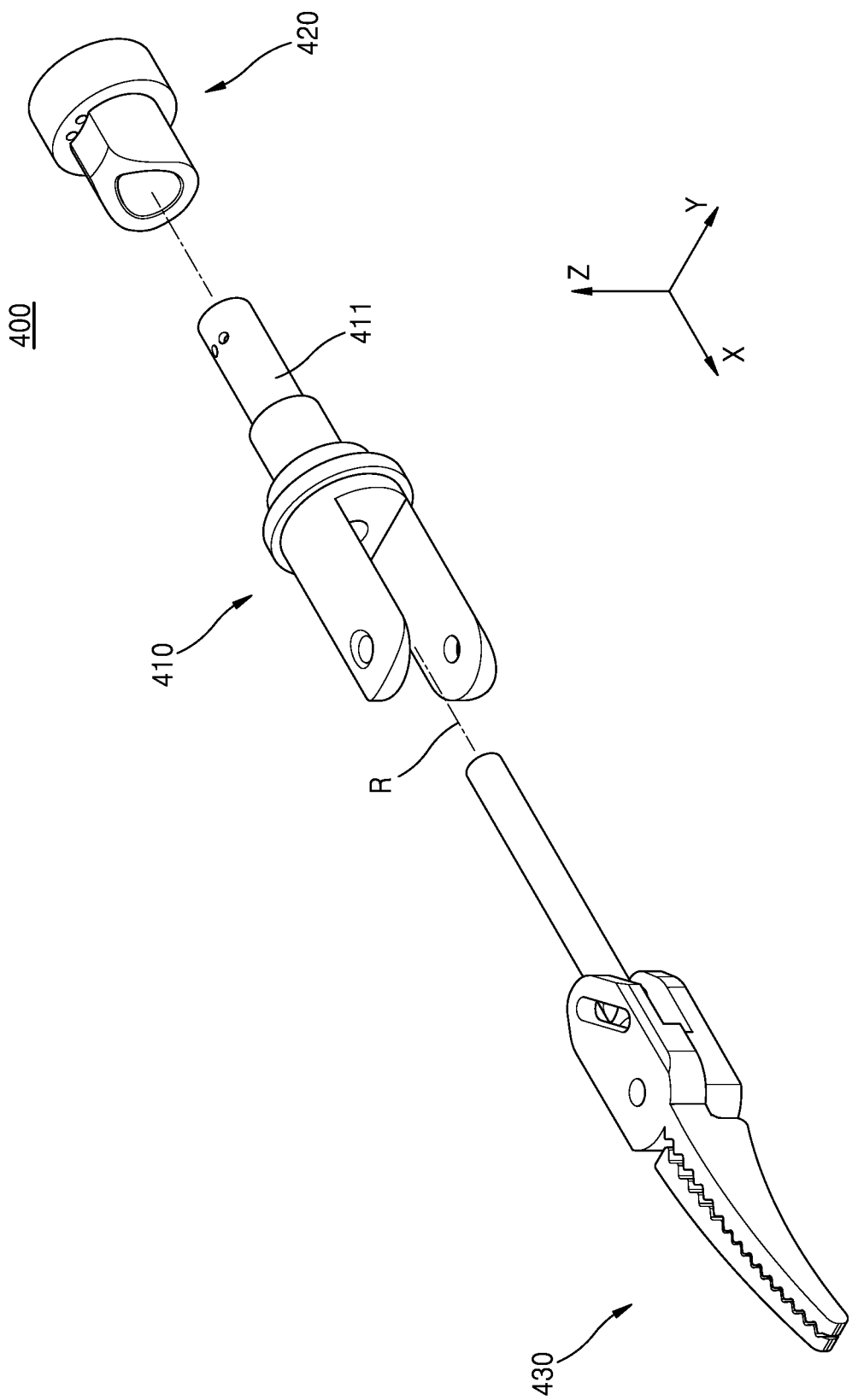
FIG. 4A is an exploded perspective view of a roll joint member according to another embodiment.
Figure 4B:
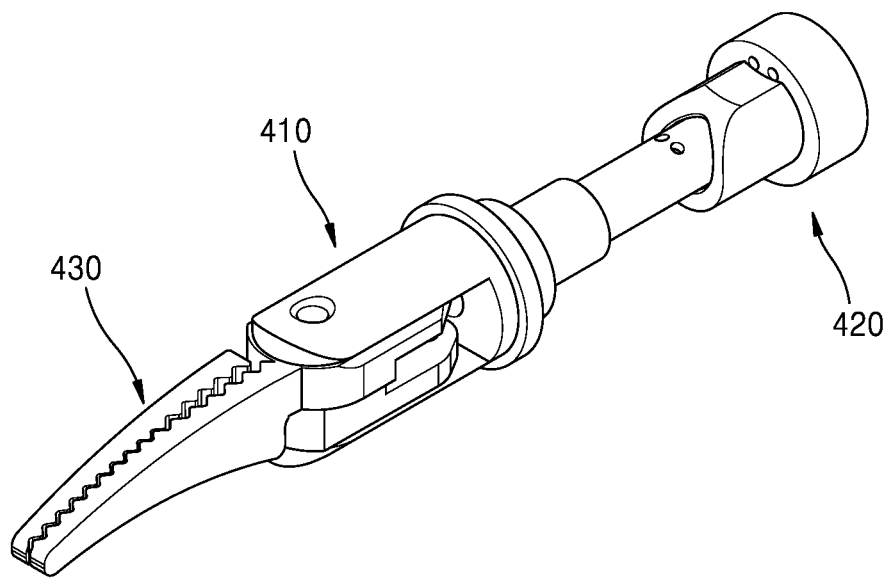
FIG. 4B is an assembled perspective view of the roll joint member of FIG. 4A.
Figure 4C:
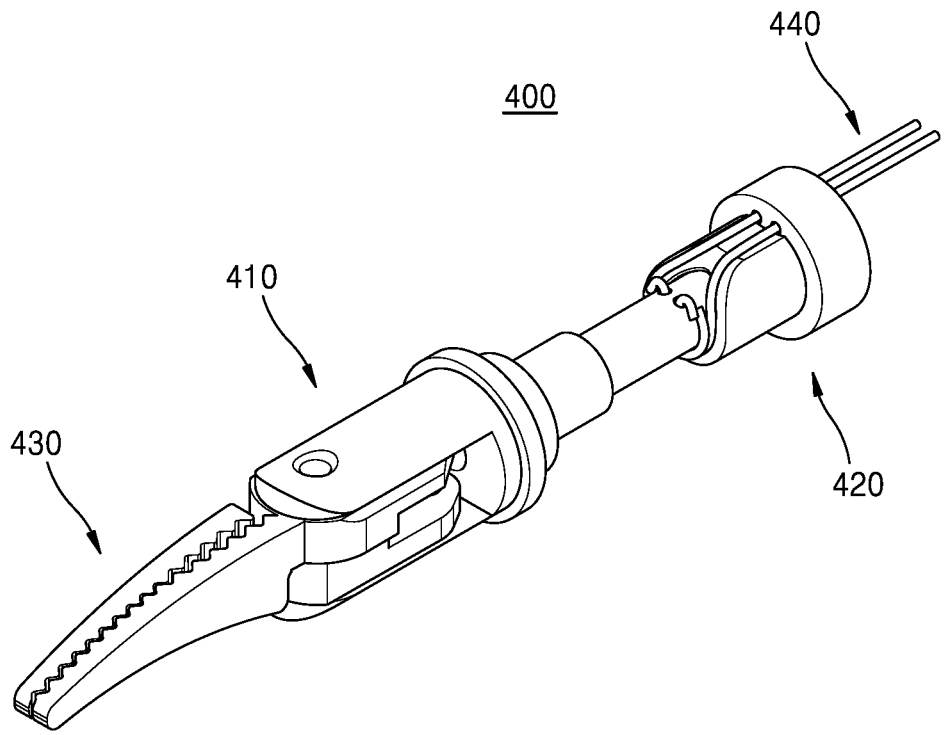
FIG. 4C is an assembled perspective view illustrating that a wire is coupled to the roll joint member of FIG. 4A.
Figure 4D:
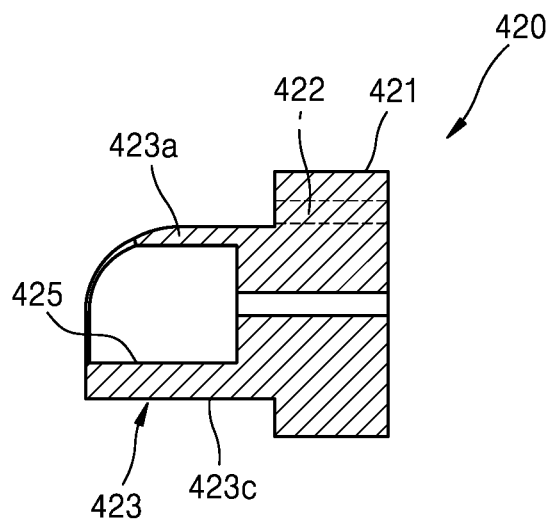
FIG. 4D is a lateral cross-sectional view of a guide member of the roll joint member of FIG. 4A.
Figure 4E:
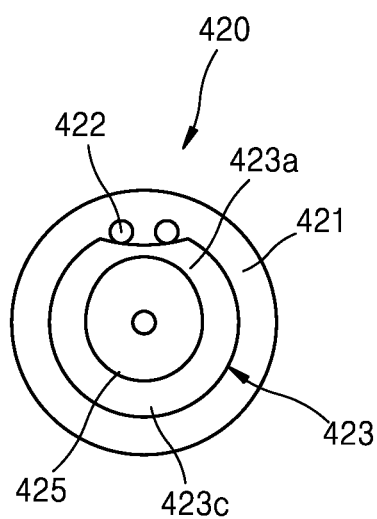
FIG. 4E is a front view of the guide member of the roll joint member of FIG. 4A.

FIG. 4A is an exploded perspective view of the roll joint member 400 according to another embodiment. FIG. 4B is an assembled perspective view of the roll joint member 400 of FIG. 4A. FIG. 4C is an assembled perspective view illustrating that a roll wire 440 is coupled to the roll joint member 400 of FIG. 4A. FIG. 4D is a lateral cross-sectional view of the guide member 420 of the roll joint member 400 of FIG. 4A. FIG. 4E is a front view of the guide member 420 of the roll joint member 400 of FIG. 4A.

Referring to FIGS. 4A to 4E, the roll joint member 400 for the surgical instrument 1 according to the present embodiment may include a shaft member 410 and the guide member 420. In this state, an end tool 430 is coupled to one end portion of the shaft member 410, and the connection portion 103 of the surgical instrument 1 of FIG. 1 is coupled to one end portion of the guide member 420. The roll wire 440 having one end portion fixedly coupled to the shaft member 410 penetrates the guide member 420 and extends toward the connection portion 103 of FIG. 1 and the manipulation portion. In the following description, the guide member 420 is described in detail.

The guide member 420 may include a housing 421 and a guide portion 423.

The guide portion 423 may be formed in a hollow shape. Accordingly, a shaft hole 425 may be formed in the housing 421 and the guide portion 423, and a shaft 411 of the shaft member 410 may be rotatably coupled to the shaft hole 425.

The guide portion 423 may include a wire guide portion 423a and a wire support portion 423c.

The wire guide portion 423a guides a path of the roll wire 440 that penetrates a wire hole 422.

The wire support portion 423c may support at least a part of the roll wire 440. In other words, when the roll wire 440 wound around the shaft member 410 is wound around the wire guide portion 423a by changing a winding direction, the wire support portion 423c may support the roll wire 440 such that the roll wire 440 is stably wound around the shaft member 410.

Referring to FIGS. 4D and 4E, in the roll joint member 400 according to the present embodiment, the wire guide portion 423a and the wire support portion 423c are characteristically formed such that, when viewed on a plane perpendicular to the roll axis R, upper and lower sides (or left and right sides according to a rotation position) of the guide member 420 are asymmetrically formed with respect to the roll axis R. In other words, since the shaft member 410 and the guide member 420 are formed as separate members, even when the shaft member 410 rotates, the guide member 420 does not rotate, and thus the guide member 420 that does not rotate may be formed in an asymmetrical shape.

In this state, the wire guide portion 423a guides the path of the roll wire 440. The wire guide portion 423a may be formed to have a concave portion shape that is concavely recessed having a certain curvature. The roll wire 440 having one end portion wound around the shaft member 410 is guided toward the wire hole 422 along the concave portion of the wire guide portion 423a. In this state, tension applied to the roll wire 440 allows the roll wire 440 to closely contact a surface of the wire guide portion 423a.

In contrast, the wire support portion 423c is formed roughly in an arc or hemispherical shape and may support at least a part of a portion of the roll wire 440 wound around the shaft member 410. As such, since the wire support portion 423c is provided to support the roll wire 440 so that the roll wire 440 is stably wound around the shaft member 410, linearity or stability of a roll motion may be improved. Furthermore, since the guide member 420 does not rotate and remains fixed during a roll motion, the roll wire 440 moves forward and backward only on the path of the roll wire 440 wound around the guide member 420, and thus a frictional force between the roll wire 440 and the guide member 420 may be reduced. In other words, an additional frictional force may not be generated because the guide member 420 does not rotate in a direction different from the direction in which the roll wire 440 moves forward or backward.

As such, since the shaft member 410 and the guide member 420 are formed as separate members, the shape of the guide member 420 may be asymmetrically formed without being limited by axial symmetry. Accordingly, the shape of the guide member 420 may be manufactured according to an optimal path of the roll wire 440 suitable for the roll motion of the surgical instrument 1. Furthermore, when the roll wire 440 wound around the shaft member 410 is wound around the guide member 420 by changing the winding direction, the wire support portion 423c may support the roll wire 440 to be stably wound around the shaft member 410. Also, according to the above structure, the rotation of the shaft member 410 due to the roll motion may not affect the winding shape of the roll wire 440 wound around the guide member 420.

In the following description, a roll joint member 500 for the surgical instrument 1 according to another embodiment is described below. In this state, the roll joint member 500 for the surgical instrument 1 according to the present embodiment is characteristically different from the roll joint member 100 for the surgical instrument 1 of FIG. 1A, in terms of the structure of a guide member 520. In the following description, the structure of the guide member 520 is mainly described below.

Figure 5A:
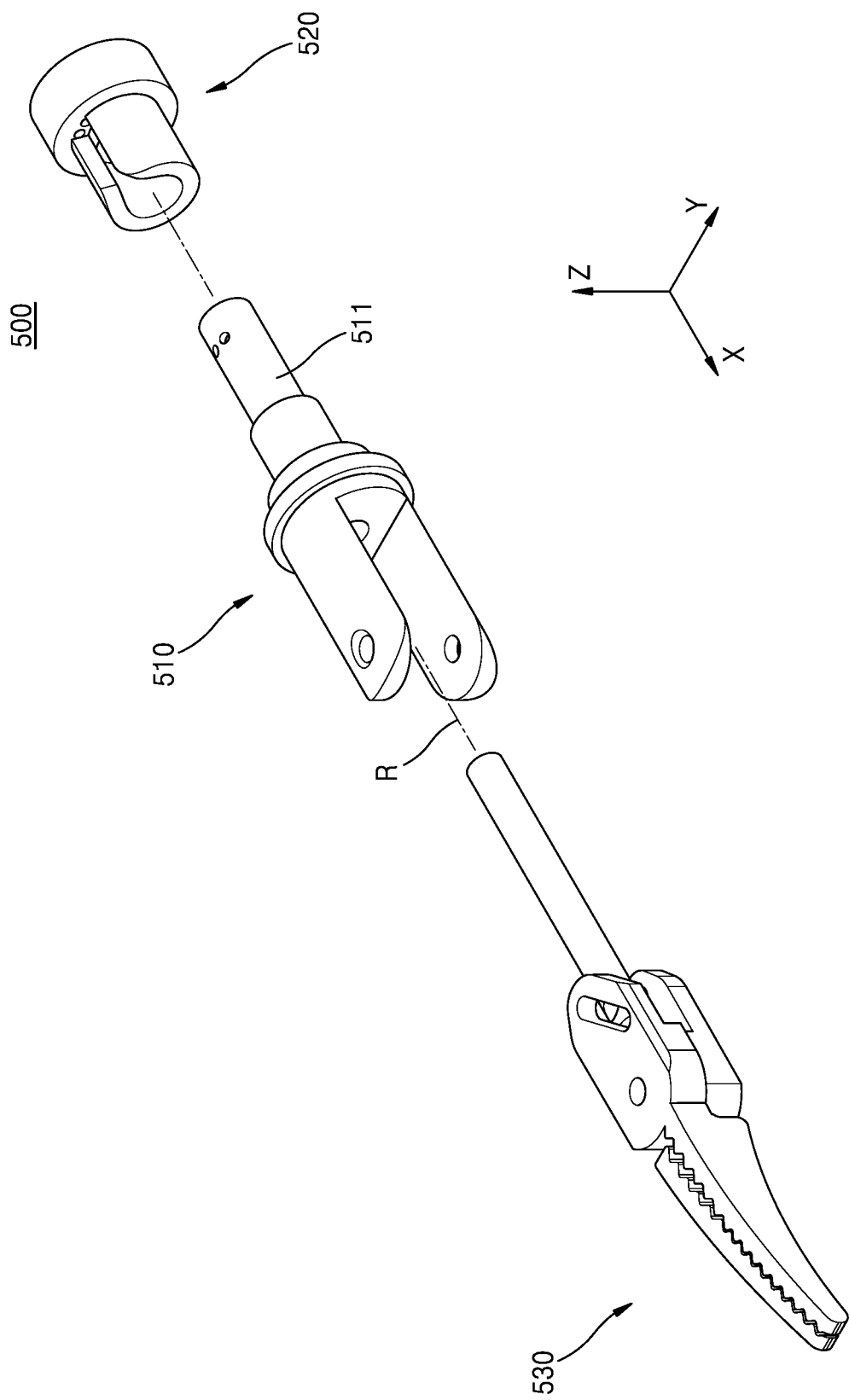
FIG. 5A is an exploded perspective view of a roll joint member according to another embodiment.
Figure 5B:
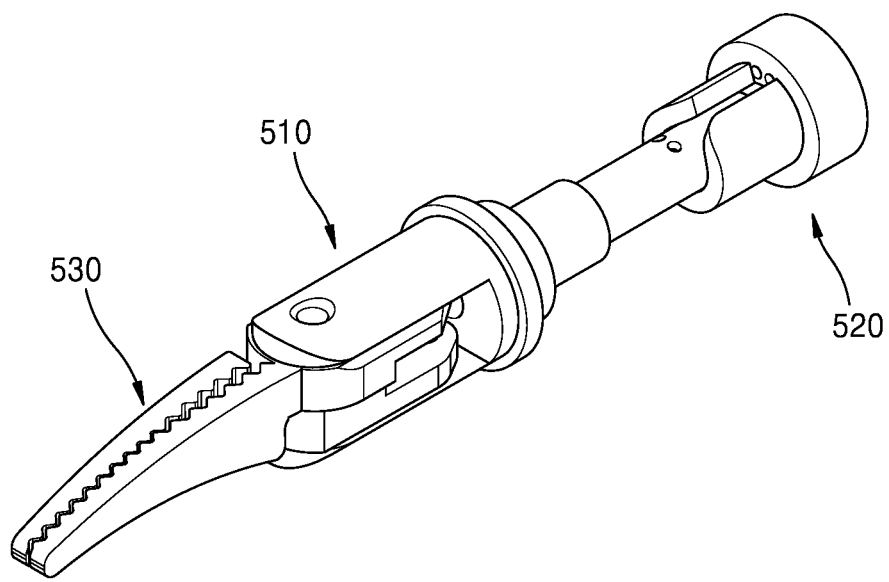
FIG. 5B is an assembled perspective view of the roll joint member of FIG. 5A.
Figure 5C:
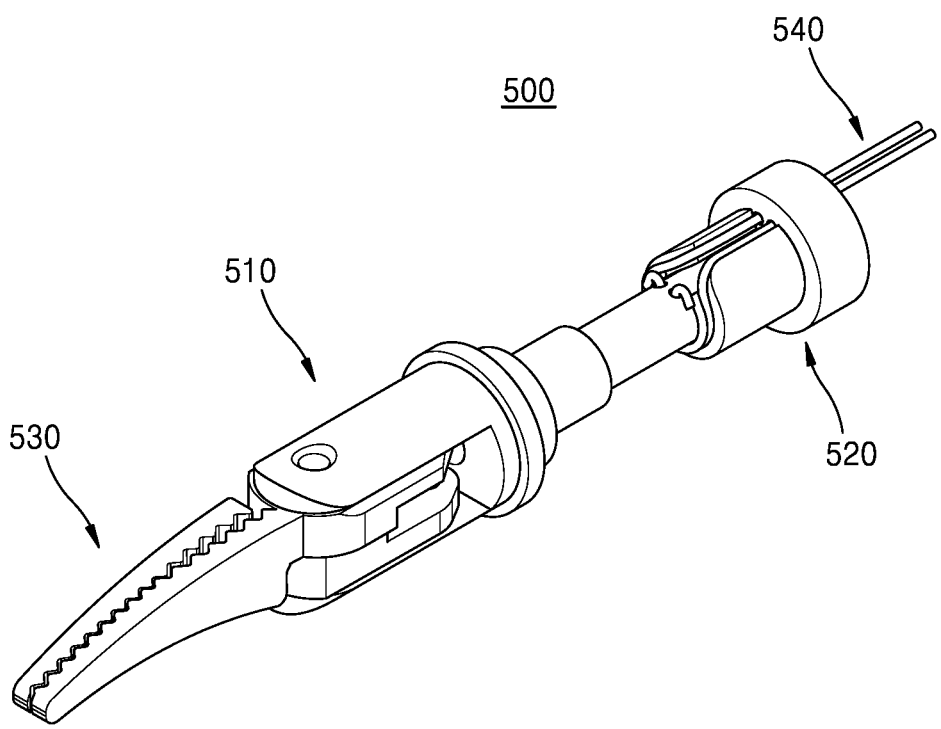
FIG. 5C is an assembled perspective view illustrating that a wire is coupled to the roll joint member of FIG. 5A.
Figure 5D:
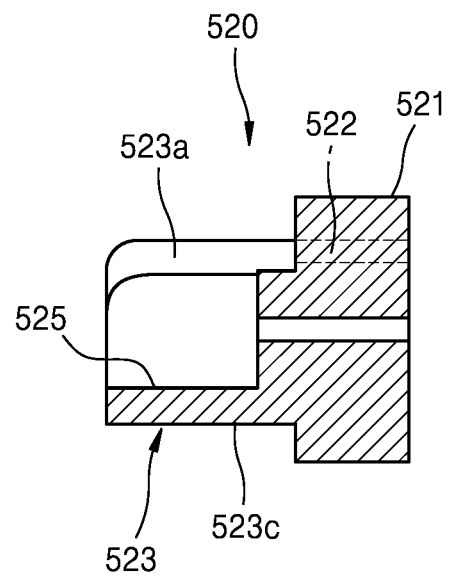
FIG. 5D is a lateral cross-sectional view of a guide member of the roll joint member of FIG. 5A.
Figure 5E:
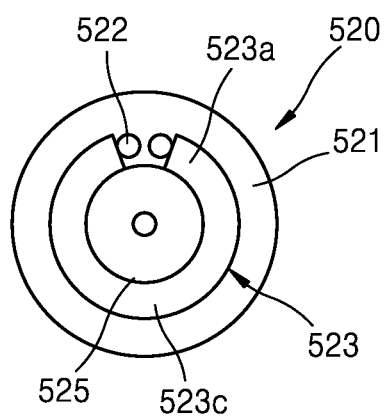
FIG. 5E is a front view of the guide member of the roll joint member of FIG. 5A.

FIG. 5A is an exploded perspective view of the roll joint member 500 according to another embodiment. FIG. 5B is an assembled perspective view of the roll joint member 500 of FIG. 5A. FIG. 5C is an assembled perspective view illustrating that a roll wire is coupled to the roll joint member 500 of FIG. 5A. FIG. 5D is a lateral cross-sectional view of the guide member 520 of the roll joint member 500 of FIG. 5A. FIG. 5E is a front view of the guide member 520 of the roll joint member 500 of FIG. 5A.

Referring to FIGS. 5A to 5E, the roll joint member 500 for the surgical instrument 1 according to the present embodiment may include a shaft member 510 and the guide member 520. In this state, an end tool 530 is coupled to one end portion of the shaft member 510, and the connection portion 103 of the surgical instrument 1 of FIG. 1 is coupled to one end portion of the guide member 520. The roll wire 540 having one end portion fixedly coupled to the shaft member 510 penetrates the guide member 520 and extends toward the connection portion 103 of FIG. 1 and the manipulation portion. In the following description, the guide member 520 is described in detail.

The guide member 520 may include a housing 521 and a guide portion 523.

The guide portion 523 may be formed in a hollow shape. Accordingly, a shaft hole 525 may be formed in the housing 521 and the guide portion 523, and a shaft 511 of the shaft member 510 may be rotatably coupled to the shaft hole 525.

The guide portion 523 may include a wire guide portion 523a and a wire support portion 523c.

The wire guide portion 523a guides a path of the roll wire 540 that penetrates a wire hole 522.

The wire support portion 523c may support at least a part of the roll wire 540. In other words, when the roll wire 540 wound around the shaft member 510 is wound around the wire guide portion 523a by changing a winding direction, the wire support portion 523c may support the roll wire 540 such that the roll wire 540 is stably wound around the shaft member 510.

Referring to FIGS. 5D and 5E, in the roll joint member 500 according to the present embodiment, the wire guide portion 523a and the wire support portion 523c are characteristically formed such that, when viewed on a plane perpendicular to the roll axis R, upper and lower sides (or left and right sides according to a rotation position) of the guide member 520 are asymmetrically formed with respect to the roll axis R. In other words, since the shaft member 510 and the guide member 520 are formed as separate members, even when the shaft member 510 rotates, the guide member 520 does not rotate, and thus the guide member 520 that does not rotate may be formed in an asymmetrical shape.

In this state, the wire guide portion 523a guides the path of the roll wire 540. The wire guide portion 523a may be formed in a shape of a cylinder having an open or cut part. In other words, a part of a cylindrical shape is cut in a roll axis direction, forming a groove, and the roll wire 540 is guided toward the wire hole 522 along the cut part. In this state, tension applied to the roll wire 540 allows the roll wire 540 to closely contact a surface of the wire guide portion 523a.

In contrast, the wire support portion 523c may be formed roughly in an arc or hemispherical shape and may support at least a part of a portion of the roll wire 540 wound around the shaft member 510. As such, since the wire support portion 523c is provided to support the roll wire 540 so that the roll wire 540 is stably wound around the shaft member 510, linearity or stability of a roll motion may be improved. Furthermore, since the guide member 520 does not rotate and remains fixed during a roll motion, the roll wire 540 moves forward and backward only on the path of the roll wire 540 wound around the guide member 520, and thus a frictional force between the roll wire 540 and the guide member 520 may be reduced. In other words, an additional frictional force may not be generated because the guide member 520 does not rotate in a direction different from the direction in which the roll wire 540 moves forward or backward.

As such, since the shaft member 510 and the guide member 520 are formed as separate members, the shape of the guide member 520 may be asymmetrically formed without being limited by axial symmetry. Accordingly, the shape of the guide member 520 may be manufactured according to an optimal path of the roll wire 540 suitable for the roll motion of the surgical instrument 1. Furthermore, when the roll wire 540 wound around the shaft member 510 is wound around the guide member 520 by changing the winding direction, the wire support portion 525c may support the roll wire 540 to be stably wound around the shaft member 510. Also, according to the above structure, the rotation of the shaft member 510 due to the roll motion may not affect the winding shape of the roll wire 540 wound around the guide member 520.

In the following description, a roll joint member 600 for the surgical instrument 1 according to another embodiment is described below. In this state, the roll joint member 600 for the surgical instrument 1 according to the present embodiment is characteristically different from the roll joint member 100 for the surgical instrument 1 of FIG. 1A, in terms of the structure of guide members 620 and 650. In the following description, the structure of the guide members 620 and 650 are mainly described below.

Figure 6A:
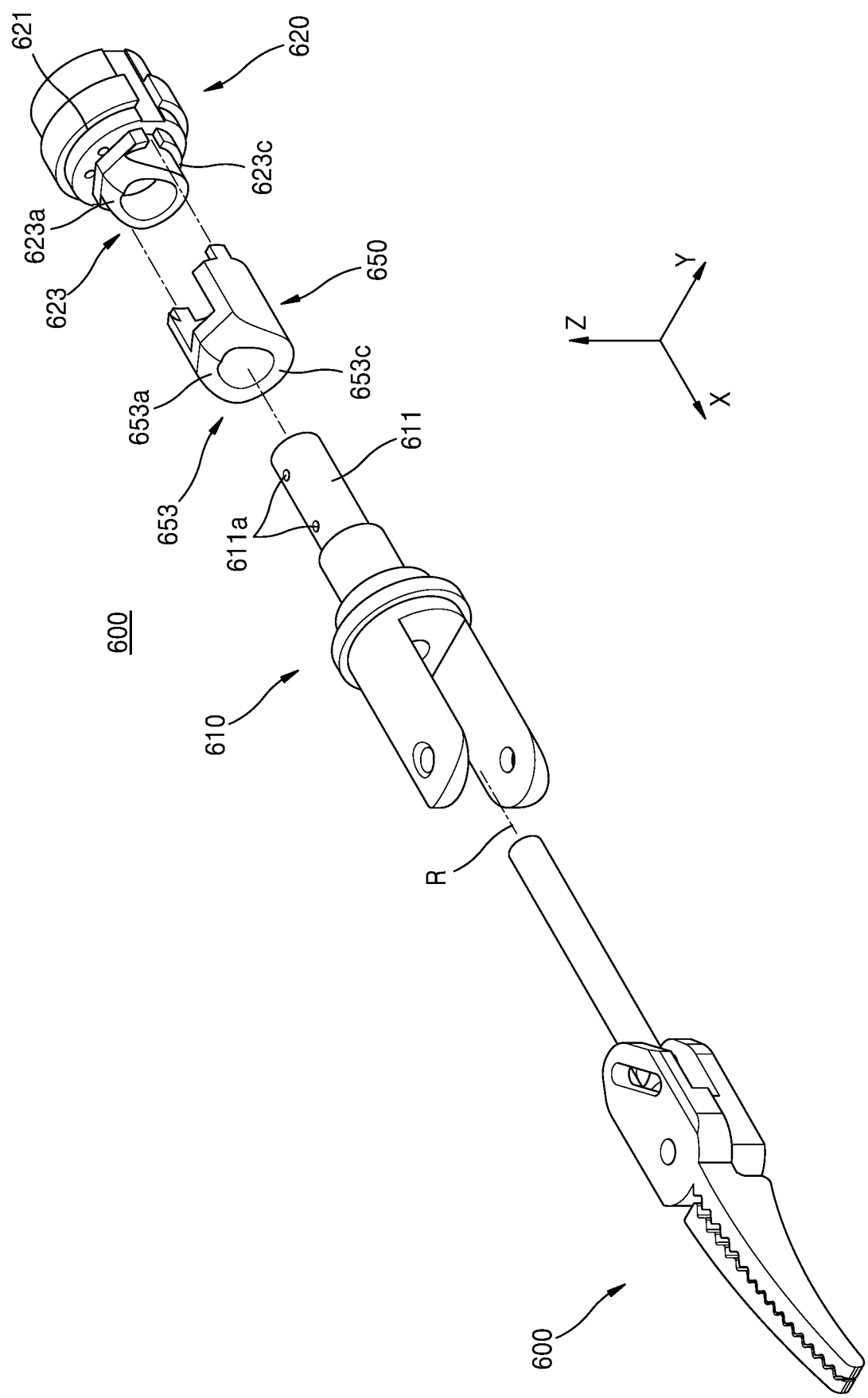
FIG. 6A is an exploded perspective view of a roll joint member according to another embodiment.
Figure 6B:
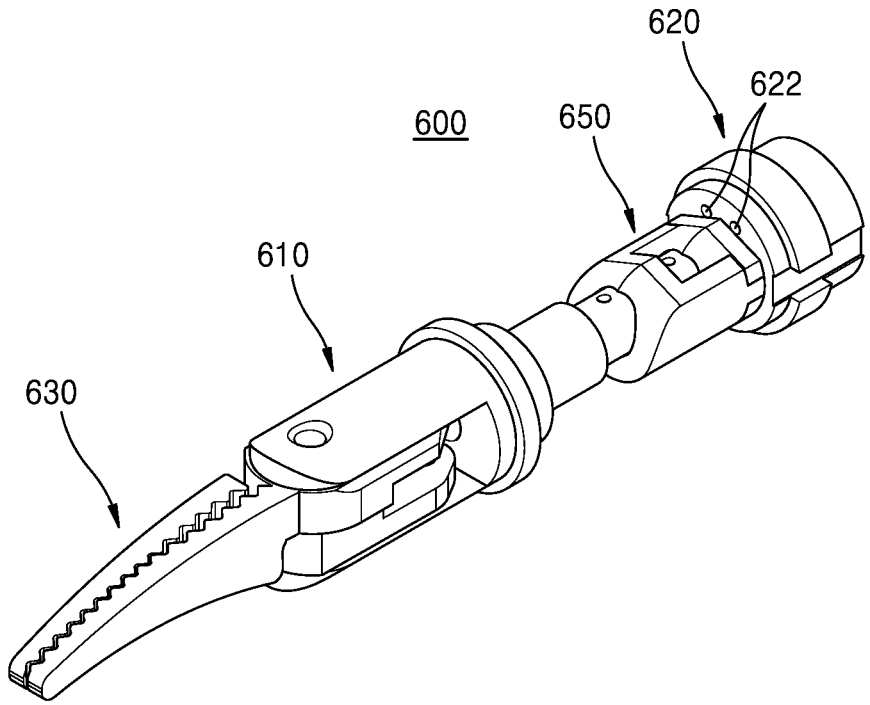
FIG. 6B is an assembled perspective view of the roll joint member of FIG. 6A.
Figure 6C:
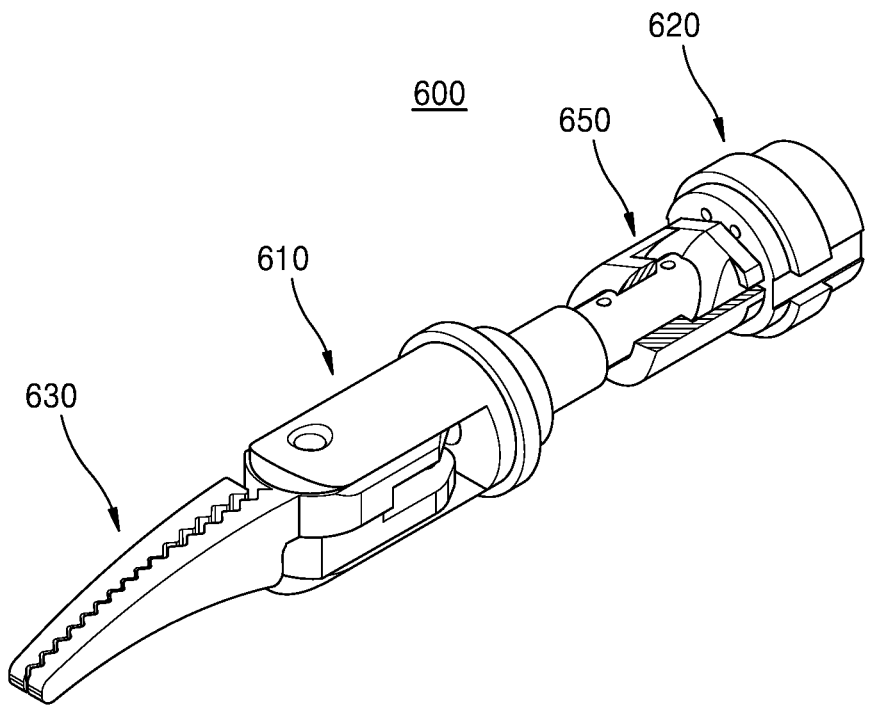
FIG. 6C is a partially cut-away assembled perspective view of the roll joint member of FIG. 6A.
Figure 6D:
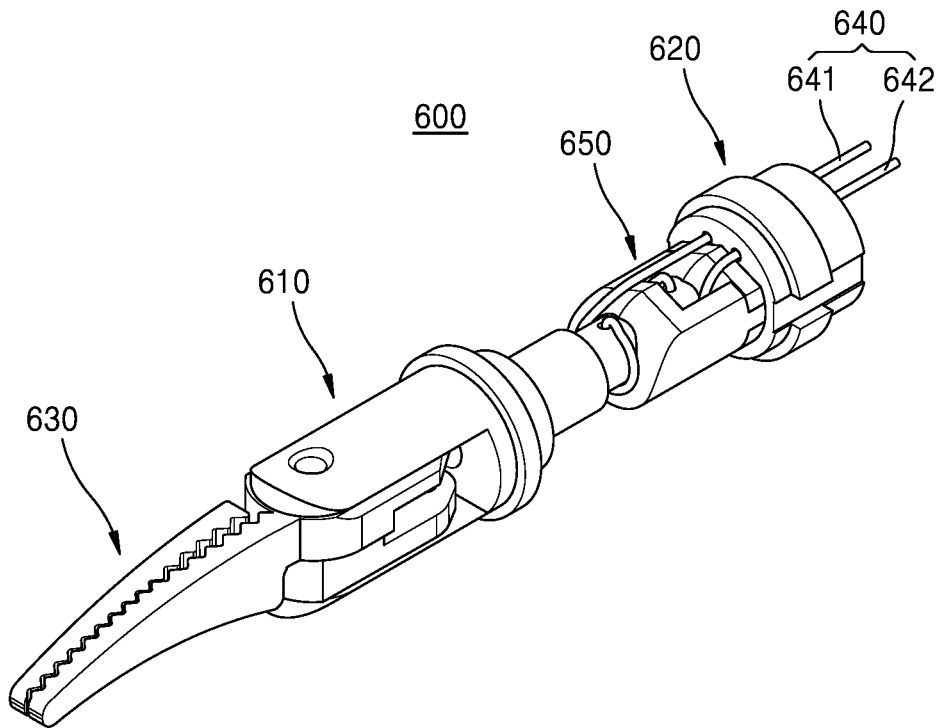
FIG. 6D is an assembled perspective view illustrating that a wire is coupled to the roll joint member of FIG. 6A.
Figure 6E:
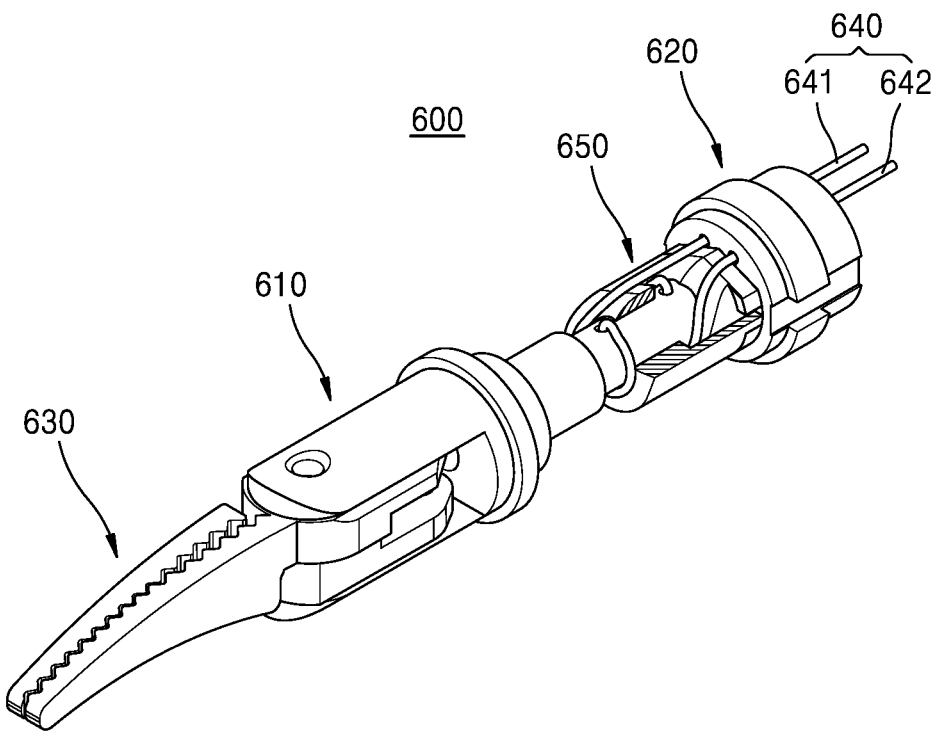
FIG. 6E is a partially cut-away assembled perspective view of the roll joint member of FIG. 6D.

FIG. 6A is an exploded perspective view of the roll joint member 600 according to another embodiment. FIG. 6B is an assembled perspective view of the roll joint member 600 of FIG. 6A. FIG. 6C is a partially cut-away assembled perspective view of the roll joint member 600 of FIG. 6A. FIG. 6D is an assembled perspective view illustrating that a roll wire 640 is coupled to the roll joint member 600 of FIG. 6A. FIG. 6E is a partially cut-away assembled perspective view of the roll joint member 600 of FIG. 6D.

Referring to FIGS. 6A to 6E, the roll joint member 600 for the surgical instrument 1 according to the present embodiment may include a shaft member 610, the first guide member 620, and a second guide member 650. In this state, an end tool 630 is coupled to one end portion of the shaft member 610, and the connection portion 103 of the surgical instrument 1 of FIG. 1 is coupled to one end portion of the first guide member 620. The roll wire 640 having the one end portion fixedly coupled to the shaft member 610 penetrates the first guide member 620 and extends toward the connection portion 103 of FIG. 1 and the manipulation portion.

In this state, in the roll joint member 600 for the surgical instrument 1 according to the present embodiment, since the guide member 620 is formed as two separate members of the first guide member 620 and the second guide member 650, a first roll wire 641 and a second roll wire 642 may be prevented from interfering with each other. In the following description, the first guide member 620 and the second guide member 650 are described in detail.

The first guide member 620 may include a housing 621 and a guide portion 623.

In this state, since the first guide member 620 is substantially the same as the guide member 120 of FIG. 1A, except that a coupling portion is formed for the coupling of the second guide member 650, a detailed description thereof is omitted. The guide members according to other embodiments may be used as the first guide member 620.

The second guide member 650 may be formed in a hollow shape. A shaft 611 of the shaft member 610 may be rotatably coupled to the second guide member 650. The second guide member 650 may be inserted into the first guide member 620. The second guide member 650 may be similar to a shape of the first guide member 620 without the housing 621.

The second guide member 650 may include a wire guide portion 653a and a wire support portion 653c. The wire guide portion 653a guides the path of the roll wire 640 that penetrates a wire hole (622). The wire support portion 653c may support at least a part of the roll wire 640. In other words, when the roll wire 640 wound around the shaft member 610 is wound around the wire guide portion 623a by changing a winding direction, the wire support portion 623c may support the roll wire 640 such that the roll wire 640 is stably wound around the shaft member 610.

In this state, the first guide member 620 and the second guide member 650 are formed as separate members. Both of the first roll wire 641 and the second roll wire 642 are coupled to the shaft member 610. The differences between the present embodiment and the above-described embodiments lie in that two wire coupling holes 611a formed in the shaft member 610 are formed along the roll axis R, not crossing the roll axis R. The second roll wire 642 may be supported and guided by a guide member 653 of the first guide member 620.

In this state, the first roll wire 641 and the second roll wire 642 are formed as separate wires, and one end portion of each of the first roll wire 641 and the second roll wire 642 may be fixedly coupled to the shaft member 610, or the first roll wire 641 and the second roll wire 642 may be one wire (connected to each other) and a center point (or connection point) thereof may be fixedly coupled to the shaft member 610.

According to the above structure, since the first roll wire 641 and the second roll wire 642 are formed not to contact and interfere with each other, the roll motion may be stably and surely implemented.

As described above, accuracy of the roll motion may be improved by the roll joint member for a surgical instrument according to the present disclosure.

The particular implementations shown and described herein are illustrative examples of the disclosure and are not intended to otherwise limit the scope of the disclosure in any way. For the sake of brevity, conventional electronics, control systems, software development and other functional aspects of the systems may not be described in detail. Furthermore, the connecting lines, or connectors shown in the various figures presented are intended to represent functional relationships and/or physical or logical couplings between the various elements. It should be noted that many alternative or additional functional relationships, physical connections or logical connections may be present in a practical device. Moreover, no item or component is essential to the practice of the disclosure unless the element is specifically described as "essential" or "critical."

The use of the terms "a" and "an" and "the" and similar referents in the context of describing the disclosure (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The present disclosure is not limited to the described order of the steps. The use of any and all examples, or language (e.g., "such as") provided herein, is intended merely to better illuminate the disclosure and does not pose a limitation on the scope of the disclosure unless otherwise claimed. Numerous modifications and adaptations will be readily apparent to one of ordinary skill in the art without departing from the spirit and scope of the present disclosure.

The embodiments of the present disclosure can be written as computer programs and can be implemented in general-use digital computers that execute the programs using a computer-readable recording medium. In this state, the computer-readable recording medium may continuously store a program that can be executed by a computer, or may store a program for execution or download. Furthermore, the computer-readable recording medium may be various recording devices or storing devices in which single or several hardware are combined, but it is not limited to a medium that is directly accessed by a computer system and may be present over a network in a distribution manner. Examples of the computer-readable recording medium include magnetic storage media such as floppy disks or hard disks, optical recording media such as CD-ROMs or DVDs, magneto-optical media such as floptical disks, ROM, RAM, flash memory, etc., which are configured to store program instructions. Furthermore, examples of other media may include application stores for distributing applications, sites for supplying or distributing other various software, and recording media or storing media managed at servers.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A roll joint device for a surgical instrument, the roll joint device comprising:
    a shaft member having a shaft to which at least one roll wire is coupled and rotatable around a roll axis according to a movement of the at least one roll wire; and
    a guide member having one side to which the shaft member rotatable around the roll axis is coupled,
    wherein the guide member comprises:
    at least one wire hole through which the at least one roll wire passes,
    a wire guide portion formed to contact at least a part of the at least one roll wire to guide an entry path of the at least one roll wire into the at least one wire hole such that an entry direction of the at least one roll wire into the at least one wire hole and an exit direction of the at least one roll wire from the at least one wire hole are substantially in parallel with an extension direction of the shaft, and
    a wire support portion supporting at least a part of the at least one roll wire wound around the shaft member,
    wherein the shaft member is rotatable with respect to the guide member, and wherein a radius of the wire support portion is larger than a radius of the shaft.

2. The roll joint device of claim 1, wherein the guide member and the shaft member are formed as separate members and coupled to each other.

3. The roll joint device of claim 1, wherein the wire guide portion and the wire support portion of the guide member are asymmetrically formed, when viewed on a plane perpendicular to the roll axis.

4. The roll joint device of claim 1, wherein the guide member comprises:
    a housing having a hollow shape and comprising one end portion to which a connection portion of the surgical instrument is coupled, and
    a guide portion formed at another end portion of the housing and comprising the wire guide portion and the wire support portion.

5. The roll joint device of claim 4,
    wherein the wire guide portion is configured to guide a path of the at least one roll wire that penetrates the at least one wire hole.

6. The roll joint device of claim 4, wherein the wire guide portion is formed to be inwardly recessed from the guide portion, and
    the wire guide portion is formed along a recessed surface.

7. The roll joint device of claim 4, wherein the wire guide portion is formed by opening or cutting a part of the guide portion, and
    the wire support portion has an arc shape having a predetermined central angle, when viewed on a plane perpendicular to the roll axis.

8. The roll joint device of claim 1, wherein the wire guide portion comprises two inclined surfaces forming a predetermined angle, when viewed on a plane perpendicular to the roll axis, and
    the wire support portion has an arc shape having a predetermined central angle, when viewed on a plane perpendicular to the roll axis.

9. The roll joint device of claim 1, wherein the wire guide portion comprises a flat plane, when viewed on a plane perpendicular to the roll axis, and
    the wire support portion has an arc shape having a predetermined central angle, when viewed on a plane perpendicular to the roll axis.

10. The roll joint device of claim 1, wherein the wire guide portion is concavely recessed having a curvature, when viewed on a plane perpendicular to the roll axis, and
the wire support portion has an arc shape having a predetermined central angle, when viewed on a plane perpendicular to the roll axis.

11. The roll joint device of claim 1, wherein the guide member comprises:
a first guide member having one end portion to which a connection portion of the surgical instrument is coupled; and
a second guide member having one side to which the shaft member is coupled and another side to which the first guide member is coupled,
wherein each of the first guide member and the second guide member includes the wire guide portion and the wire support portion, and
wherein a first roll wire of the at least one roll wire is supported and guided by the second guide member, and a second roll wire of the at least one roll wire is supported and guided by the first guide member.

12. The roll joint device of claim 1, wherein in a state in which the shaft member is fitted in the guide member, a stepped region is formed where the shaft member contacts the wire support portion of the guide member, and
wherein after at least a part of the at least one roll wire is wound around the shaft, while being supported by the wire support portion in the stepped region, the at least one roll wire is configured to be introduced into the at least one wire hole along a surface of the wire guide portion.

13. The roll joint device of claim 1, wherein the shaft member and the guide member are formed as separate members and coupled to each other,
wherein the shaft member is configured to rotate with respect to the guide member while the guide member is fixed, and
wherein, when viewed on a plane perpendicular to the roll axis, the wire guide portion and the wire support portion are asymmetrically formed to have different shapes from each other.

* * * * *